United States Patent
Custelcean et al.

(10) Patent No.: US 10,633,332 B2
(45) Date of Patent: Apr. 28, 2020

(54) GUANIDINE COMPOUNDS FOR REMOVAL OF OXYANIONS FROM AQUEOUS SOLUTIONS AND FOR CARBON DIOXIDE CAPTURE

(71) Applicant: UT-Battelle, LLC, Oak Ridge, TN (US)

(72) Inventors: Radu Custelcean, Beavercreek, OH (US); Charles A. Seipp, Beavercreek, OH (US); Neil J. Williams, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 16/129,979

(22) Filed: Sep. 13, 2018

(65) Prior Publication Data
US 2019/0010118 A1  Jan. 10, 2019

Related U.S. Application Data

(62) Division of application No. 15/813,557, filed on Nov. 15, 2017.

(Continued)

(51) Int. Cl.
*C07C 279/12* (2006.01)
*C02F 1/52* (2006.01)
(Continued)

(52) U.S. Cl.
CPC ........ *C07C 279/12* (2013.01); *B01D 53/1425* (2013.01); *B01D 53/1475* (2013.01);
(Continued)

(58) Field of Classification Search
None
See application file for complete search history.

(56) References Cited

U.S. PATENT DOCUMENTS 4,120,789 A * 10/1978 Fusco ............... C02F 1/5272
                                                            210/729
9,260,326 B2    2/2016 Custelcean et al.
(Continued)

FOREIGN PATENT DOCUMENTS

WO    WO 00/69973    * 11/2000

OTHER PUBLICATIONS

Levafix® Goldgelb: National Center for Biotechnology Information. PubChem Database. RKJMCSDTNRZEKD-UHFFFAOYSA-N, CID=58506738, https://pubchem.ncbi.nlm.nih.gov/compound/58500738 (accessed on Apr. 10, 2019) (Year: 2019).*

(Continued)

*Primary Examiner* — Amy C Bonaparte
(74) *Attorney, Agent, or Firm* — Scully Scott Murphy & Presser, P.C.

(57) ABSTRACT

Methods for removing oxyanions from water according to the following steps: (i) dissolving an oxyanion precipitating compound into the aqueous source to result in precipitation of an oxyanion salt of the oxyanion precipitating compound; and (ii) removing the oxyanion salt from the water containing the oxyanion to result in water substantially reduced in concentration of the oxyanion; wherein the oxyanion precipitating compound has the following composition:

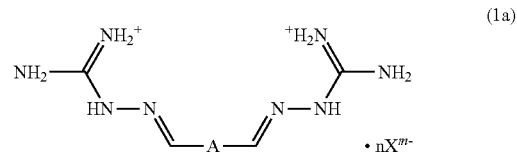

wherein A is a ring-containing moiety and $X^{m-}$ is an anionic species with a magnitude of charge m. The invention (Continued)

employs bis-iminoguanidinium compounds according to Formula (1a) as well as neutral precursor compounds according to Formula (1), which can be used for removing undesirable species from aqueous solutions or air, such as removal of sulfate from water and carbon dioxide from air.

22 Claims, 11 Drawing Sheets

Related U.S. Application Data

(60) Provisional application No. 62/422,138, filed on Nov. 15, 2016, provisional application No. 62/459,118, filed on Feb. 15, 2017, provisional application No. 61/422,142, filed on Dec. 11, 2010, provisional application No. 62/514,997, filed on Jun. 5, 2017.

(51) Int. Cl.

| | | |
|---|---|---|
| *B01D 53/14* | (2006.01) | |
| *C07C 281/18* | (2006.01) | |
| *C07D 333/22* | (2006.01) | |
| *C07D 239/26* | (2006.01) | |
| *C07D 241/12* | (2006.01) | |
| *C07D 207/335* | (2006.01) | |
| *C07D 213/53* | (2006.01) | |
| *C07D 307/52* | (2006.01) | |
| *C07D 213/00* | (2006.01) | |
| *C02F 103/08* | (2006.01) | |
| *C02F 101/10* | (2006.01) | |

(52) U.S. Cl.
CPC ........ *B01D 53/1493* (2013.01); *C02F 1/5272* (2013.01); *C07C 281/18* (2013.01); *C07D 207/335* (2013.01); *C07D 213/00* (2013.01); *C07D 213/53* (2013.01); *C07D 239/26* (2013.01); *C07D 241/12* (2013.01); *C07D 307/52* (2013.01); *C07D 333/22* (2013.01); *B01D 2252/20415* (2013.01); *B01D 2252/20421* (2013.01); *B01D 2252/20426* (2013.01); *B01D 2252/20431* (2013.01); *B01D 2252/20457* (2013.01); *B01D 2252/20494* (2013.01); *B01D 2258/06* (2013.01); *C02F 2101/101* (2013.01); *C02F 2101/103* (2013.01); *C02F 2101/105* (2013.01); *C02F 2103/08* (2013.01); *C07C 2601/16* (2017.05); *Y02C 10/06* (2013.01); *Y02E 50/346* (2013.01); *Y02P 20/152* (2015.11); *Y02W 10/37* (2015.05)

(56) References Cited

U.S. PATENT DOCUMENTS

| | | |
|---|---|---|
| 2003/0219440 A1 | 11/2003 | Tobia et al. |
| 2017/0081223 A1 | 3/2017 | Hull et al. |
| 2018/0345207 A1* | 12/2018 | Custelcean ........ B01D 53/1475 |

OTHER PUBLICATIONS

Levafix® Brilliant Red E-4BA: National Center for Biotechnology Information. PubChem Database. AKNCRKIUQODFJV-UHFFFAOYSA-N, CID=101239371, https://pubchem.ncbi.nlm.nih.gov/compound/101239371 (accessed on (Year: 2019).*

Procion® Orange MX2R: National Center for Biotechnology Information. PubChem Database. Procion orange MX-2R, CID=93408, https://pubchem.ncbi.nlm.nih.gov/compound/93408 (accessed on Apr. 10, 2019) (Year: 2019)*

Reactive Black 5 (Sigma Aldrich product page, downloaded from https://www.sigmaaldrich.com/catalog/product/sial/306452?lang=en&region=US on Apr. 10, 2019) (Year: 2019).*

Custelcean R. et al., "Aqueous sulfate separation by crystallization of sulfate-water clusters", Angew. Chem. Int. Ed., 2015, 54, pp. 10525-10529.

Custelcean R. et al., "Aqueous sulfate separation by sequestration of [(SO4)2(H2O)4]4-clusters within highly insoluble imine-linked bis-guanidinium crystals", Chem. Eur. J., 2016, 22, pp. 1997-2003.

Ulrich P.C. et al., "The Trypanocidal Activity of Various Aromatic Bisguanylhydrazones In Vivo", Drug Development Research, 1982, 2, pp. 219-228.

French F.A. et al., "Chemotherapy Studies on Transplanted Mouse Tumors", Cancer Research, 1960, 20, pp. 505-538.

Berge S.M. et al., "Pharmaceutical Salts", Journal of Pharmaceutical Sciences, 1977, 66, pp. 1-19.

Knownium K. et al., "Novel endotoxin-sequestering compounds with terephthalaldehyde-bis-guanylhydrazone scaffolds" Bioorganic & Medicinal Chemistry Letters, 2006, 16, pp. 1305-1308.

* cited by examiner

GUANIDINE COMPOUNDS FOR REMOVAL OF OXYANIONS FROM AQUEOUS SOLUTIONS AND FOR CARBON DIOXIDE CAPTURE

CROSS REFERENCE TO RELATED APPLICATION

The present application is a divisional of U.S. Ser. No. 15/813,557, filed Nov. 15, 2017, which claims benefit of U.S. Provisional Application No. 62/422,138, filed on Nov. 15, 2016, U.S. Provisional Application No. 62/459,118, filed on Feb. 15, 2017, U.S. Provisional Application No. 61/422, 142, filed on Nov. 15, 2016, and U.S. Provisional Application No. 62/514,997, filed on Jun. 5, 2017, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention generally relates to compositions useful for removing undesirable species from aqueous solutions or air, such as removal of sulfate from water and carbon dioxide from air, and to methods for using such materials in removing such species.

BACKGROUND OF THE INVENTION

Effective separation of highly hydrophilic anions (e.g., sulfate, selenate, chromate, phosphate) from competitive aqueous solutions remains a major challenge, despite the tremendous progress in anion receptor chemistry over the past decade. In the particular case of sulfate, although a significant number of sulfate-binding receptors have been reported (e.g., I. Ravikumar et al., *Chem. Soc. Rev.*, 41, 3077, 2012), they have shown limited success in the substantial removal of this anion from water. A significant obstacle in the development of anion receptors is often the multi-step synthesis required for their assembly, which generally involves tedious purifications and the use of toxic reagents and solvents.

The removal of sulfate from seawater, in particular, continues to be an ongoing challenge. Seawater contains very high levels of sulfate (~3,000 mg/L), and seawater is used on a large scale in oil-field injection operations. During such operations, the sulfate in the seawater combines with strontium and barium found in rock to form barium and strontium sulfate scale. The precipitation of barium and strontium sulfates is highly detrimental to the process, such as by clogging lines and destroying production wells. The conventional technology for removing sulfate from seawater is by nanofiltration, which can reduce sulfate levels to about 50 mg/mL. However, some drawbacks to this approach are the remaining high sulfate levels, the need to pressurize the system to 20-30 bars, which results in a significant expenditure in energy, and membrane fouling. Other methods involve scale-removing chemicals, but these are known to be difficult to use and very expensive, and are not very effective against sulfate scales. Another technology, known as the MD-LPP process, yields sulfate-free seawater, but the process has the significant drawbacks of employing high pressures, pre-concentrating the sea water, and use of organic solvents.

An approach for aqueous anion separation that has proven particularly effective is selective anion crystallization with organic compounds functionalized with hydrogen bonding groups (e.g., a) R. Custelcean, *Curr. Opin. Solid State Mater. Sci.* 2009, 13, 68; b) R. Custelcean, *Chem. Soc. Rev.* 2010, 39, 3675; c) R. Custelcean, *Chem. Commun.* 2013, 49, 2173). This approach combines elements of anion receptor chemistry and crystal engineering, as it entails recognition of the targeted anion through complementary hydrogen bonding, and formation of stable crystals through favorable packing. The challenge with anion crystallization from water is to identify anion-binding compounds that can effectively compete against the strong anion hydration, and that are also able to self-assemble with the anions of interest into crystals with low aqueous solubility. In this respect, it has recently been discovered that crystallization of sulfate, in the form of extended $[SO_4(H_2O)_5^{2-}]_n$ clusters, with rigid and planar bis-guanidinium compounds, can strike a favorable energetic balance that allows for the efficient separation of the highly hydrophilic sulfate anion from water (R. Custelcean et al., *Angew. Chem. Int. Ed.* 54, 10525, 2015; *Angew. Chem.* 127, 10671, 2015). In the foregoing prototype, the bis-guanidinium compound was synthesized in situ by condensation of glyoxal with aminoguanidinium sulfate, resulting in a sulfate salt with low aqueous solubility ($K_{sp}$=3.2×10$^{-7}$), comparable with that of $SrSO_4$. Although the solubility of the foregoing bis-guanidinium sulfate salt is much lower than many other organic sulfate salts, the solubility remains unacceptably high, particularly for use in oil-field injection operations involving competitive aqueous solutions of high ionic strength, such as seawater. There would be a significant benefit in a straight-forward and cost-efficient process that could remove substantially all sulfate from seawater without the use of pressure, nanofiltration, pre-concentration, and organic solvents.

SUMMARY OF THE INVENTION

In one aspect, the instant disclosure describes a process for removing an oxyanion (e.g., sulfate) from a aqueous source by contacting the aqueous source with specialized bis-iminoguanidinium compounds that form a highly insoluble salt of the oxyanion, thereby precipitating a substantial amount or substantially all of the oxyanion in the water. A particularly special aspect of the specialized bis-iminoguanidinium compounds described herein is the presence of a central ring-containing portion, such as a benzene or pyridine ring. By removal of the oxyanion salt, such as by filtration, the oxyanion from the water can be easily removed. The bis-iminoguanidinium compounds described herein can advantageously remove one or more oxyanions, such as sulfate, nitrate, chromate, selenate, phosphate, arsenate, carbonate, or bicarbonate, selectively or non-selectively while in the presence of other anionic species. The bis-iminoguanidinium compounds described herein can also advantageously be recycled and re-used in the oxyanion removal process. The process described herein is advantageously straight-forward and cost-efficient while at the same time removing a substantial amount or substantially all of the oxyanion from seawater or other aqueous source without requiring pressure, nanofiltration, pre-concentration, and organic solvents. The process described herein operates by simple self-assembly of the compounds and oxyanion, thereby circumventing the need for elaborate syntheses of compounds that precipitate the oxyanion directly without the aid of self-assembly.

In particular embodiments, the method for removing oxyanion from water involves the following steps: (i) dissolving an oxyanion precipitating compound into the aqueous source to result in precipitation of an oxyanion salt of the oxyanion precipitating compound; and (ii) removing the oxyanion salt from said water containing the oxyanion to result in water substantially reduced in concentration of the oxyanion; wherein the oxyanion precipitating compound has the following composition:

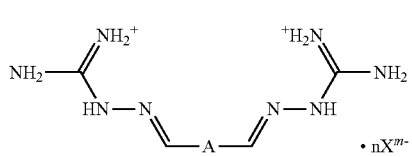

(1a)

In the above Formula (1a), A is a ring-containing moiety; $X^{m-}$ is an anionic species with a magnitude of charge m, where m is an integer of at least 1, provided that $X^{m-}$ is an anionic species exchangeable with the oxyanion in the aqueous source before the oxyanion precipitating compound contacts the oxyanion in step (i), and $X^{m-}$ is the oxyanion in the resulting oxyanion salt formed in step (i) and as separated from the water in step (ii). The subscript n is an integer of at least 1, provided that n×m=2. Moreover, one or more of the hydrogen atoms in Formula (1a), whether the hydrogen atoms are shown or not shown, may be replaced with one or more methyl groups, respectively.

In another aspect, the instant disclosure describes a process for removing carbon dioxide from a gaseous source by contacting the gaseous source with an aqueous solution containing a specialized bis-iminoguanidine compound that forms a highly insoluble salt of carbon dioxide in the form of carbonate or bicarbonate. The bis-iminoguanidine compounds described herein are analogous to the structure shown in Formula (1a), except that the bis-iminoguanidine compounds are neutral before dissolution into the aqueous solution. The structure of the neutral bis-iminoguanidine analogue is provided as follows (where A is a ring-containing moiety, as described above under Formula (1a)):

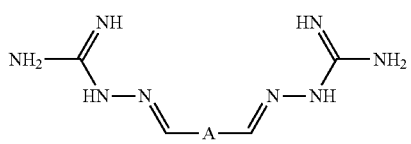

(1)

Once dissolved in aqueous solution, the bis-iminoguanidine neutral compounds react with water to form a bis-guanidinium-dihydroxide species, which corresponds to Formula (1a) when X is hydroxide (HO$^-$), i.e., with n=2 and m=1. The bis-guanidinium-dihydroxide species reacts with dissolved carbon dioxide that has been converted to carbonate or bicarbonate in the aqueous solution to form a carbonate or bicarbonate salt of the bis-iminoguanidinium compound shown in Formula (1a). In some embodiments, a liquid sorbent (e.g., a hydroxide- or amine-containing based) is first used for absorbing carbon dioxide from the gaseous source and converting the carbon dioxide to carbonate or bicarbonate. The sorbent containing the carbonate or bicarbonate is then contacted with the bis-guanidinium-dihydroxide species in aqueous solution to form a carbonate or bicarbonate salt with the bis-guanidinium species. By whichever process is used, the carbonate or bicarbonate salt of the bis-iminoguanidinium species can then be easily removed from the solution, such as by filtration. The bis-iminoguanidine compounds described herein can also advantageously be recycled and re-used in the carbon dioxide removal process. Moreover, one or more of the hydrogen atoms in Formula (1), whether the hydrogen atoms are shown or not shown, may be replaced with one or more methyl groups, respectively.

In particular embodiments, the method for removing carbon dioxide from a gaseous source involves the following steps: (i) contacting the gaseous source with an aqueous solution containing a carbon dioxide complexing compound to result in precipitation of a carbonate or bicarbonate salt of the carbon dioxide complexing compound; and (ii) removing the carbonate or bicarbonate salt from the aqueous solution. In the aqueous solution, before contact with dissolved carbon dioxide, the carbon dioxide complexing compound has the bis-guanidinium-dihydroxide composition described above, within the scope of Formula (1a). In some embodiments, the bis-guanidinium-dihydroxide composition is directly added to the aqueous solution before or during contact of the aqueous solution with the gaseous source. In other embodiments, the bis-guanidinium-dihydroxide composition is produced in situ by dissolving the neutral bis-iminoguanidine analogue according to Formula (1) into the aqueous solution.

BRIEF DESCRIPTION OF THE DRAWINGS

FIG. 1A: ORTEP representation showing the planar BBIG cation and the sulfate with the two water molecules of hydration. FIG. 1B: [(SO$_4$)$_2$(H$_2$O)$_4$]$^{4-}$ cluster. FIG. 1C: Stacking of the BBIG cations, with the dashed lines corresponding to the C═N(imine) . . . Ph and H$_2$N . . . C═N(imine) intermolecular contacts. FIG. 1D: Hydrogen bonding of the sulfate-water clusters by the guanidinium groups of the BBIG stacks, viewed down the crystallographic a axis.

FIG. 2A: ORTEP representation. FIG. 2B: Stacking of the BBIG cations. FIG. 2C: Hydrogen bonding of the nitrate anions by the guanidinium groups of the BBIG cations.

FIG. 7A: General schematic showing a direct air capture (DAC) cycle combining $CO_2$ absorption by an aqueous sorbent, crystallization of $PyBIGH_2(CO_3)(H_2O)_4$ and sorbent regeneration, and $CO_2$ release and PyBIG regeneration by heating of the carbonate crystals. FIG. 7B: Schematic diagram showing the overall $CO_2$ separation cycle in which atmospheric $CO_2$ capture using PyBIG is combined with $CO_2$ sorption by an alkali carbonate in solution.

DETAILED DESCRIPTION OF THE INVENTION

Figure 1A:
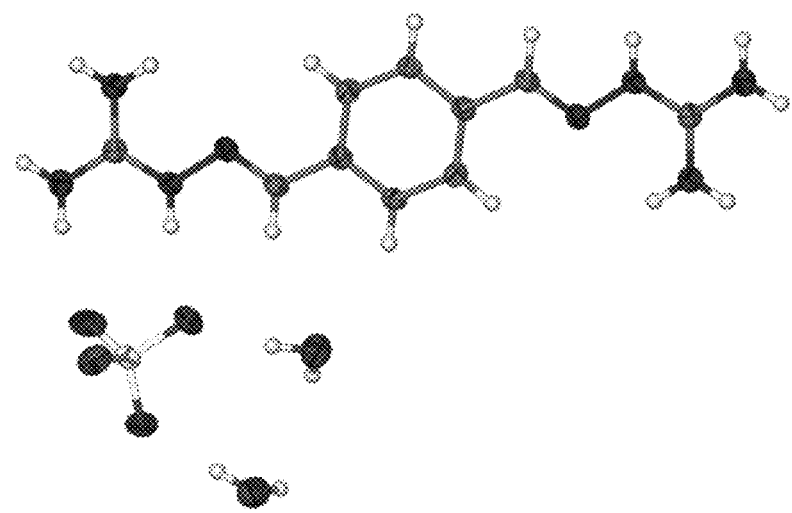
FIGS. 1A-1D. X-ray crystal structure views of 1,4-benzene-bis(iminoguanidinium) sulfate salt (BBIG-SO$_4$).

In one aspect, the invention is directed to specialized bis-iminoguanidine or bis-iminoguanidinium (i.e., "BIG") compounds having a central ring-containing moiety (A) attached to two iminoguanidine or iminoguanidinium groups. The compounds are within the scope of the following generic structure:

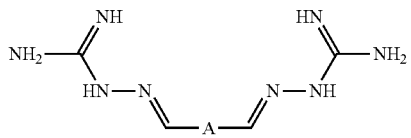

Although Formula (1) depicts a specific tautomeric arrangement, Formula (1) is intended to include any other tautomers that can be derived from or interconvert with the tautomer shown in Formula (1). As well known, tautomeric structures have the same atomic connections (aside from one or more protons) but differ in the placement of double bonds, generally with concomitant relocation of one or more protons. Some examples of tautomers of Formula (1) are provided as follows:

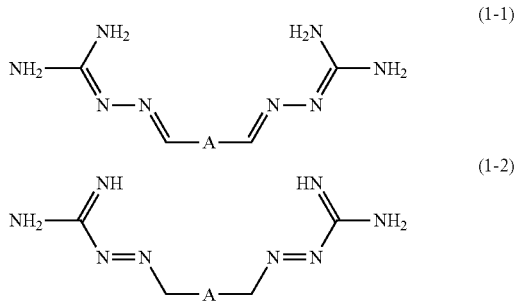

Formula (1) is also intended to include any regioisomers that may differ in the connection points of the two aminoguanidine or aminoguanidinium groups on the ring-containing moiety (A). Thus, as an example, if A is taken as a benzene (phenylene) ring, the two shown aminoguanidine or aminoguanidinium groups may be located at the 1,4 (para), 1,3 (meta) or 1,2 (ortho) positions. In some embodiments, the aminoguanidine or aminoguanidinium groups are located the farthest from each other on the ring-containing moiety. In the case of a benzene ring, the farthest positions correspond to the 1,4 (para) positions.

In the event that the structure according to Formula (1) possesses one or more stereocenters, Formula (1) is intended to include all resulting stereoisomers. The stereoisomer may include one or more enantiomers and/or diastereomers.

Moreover, although Formula (1) depicts a neutral molecule, Formula (1) is intended to encompass salt forms of the Formula (1). The salt forms generally correspond to those that can be produced by reaction of the neutral form of Formula (1) with a mineral acid or alkyl halide, which results in protonation or alkylation of one or more of the shown amine or imine groups. The salt form of Formula (1) can be expressed by the following sub-generic structure:

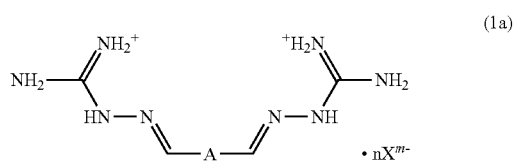

As the structure in Formula (1a) is within the scope of Formula (1), it is understood that Formula (1a), like Formula (1), includes all possible tautomers, regioisomers, and stereoisomers described above for Formula (1). Thus, the positive charge shown in Formula (1a) may be located on any of the other nitrogen atoms through tautomerizaton. As well known in the case of tautomers, the positive charge is generally distributed among all atoms capable of holding a positive charge in the various tautomers. Likewise, it is well known that partial double bond character is generally present among all of the bonds capable of engaging in double bonds in the various tautomers. Moreover, the structures in Formulas (1) and (1a) both include the possibility of one or more of the hydrogen atoms in Formula (1) or (1a), whether the hydrogen atoms are shown or not shown in the formula, being replaced with one or more methyl groups, respectively.

In Formula (1a), $X^{m-}$ is an anionic species with a magnitude of charge m, where m is an integer of at least 1, and n is an integer of at least 1, provided that n×m=2. The anionic species may be any anionic species that, when complexed as a salt with the bis-aminoguanidinium portion shown in Formula (1a), can be exchanged for another anionic species desired to be removed from an aqueous solution. As the different anionic species have different dissociation constants, any anionic species may be useful in exchanging with another anionic species to be removed from an aqueous source. The anionic species may also represent a species that has been removed from an aqueous solution, wherein the resulting salt of the removed anion and bis-aminoguanidinium portion shown in Formula (1a) is valuable as a precursor for producing a neutral form of Formula (1a) or by exchanging with another anionic species that can be used to exchange with and remove another anionic species of interest. The anionic species ($X^{m-}$) can be, for example, a halide, such as fluoride, chloride, bromide, or iodide. The anionic species can alternatively be a halide equivalent (or pseudohalide), such as methanesulfonate (mesylate), trifluoromethanesulfonate (triflate), tosylate, cyanate, thiocyanate, cyanide, or a sulfonamide anion, such as bis(trifluoromethane)sulfonamide (i.e., bistriflimide). The anionic species may alternatively be a borate anion, such as tetrafluoroborate, tetrakis(pentafluorophenyl)borate, or tetrakis[3,5-bis(trifluoromethyl)phenyl]borate. The anionic species may alternatively be hexafluorophosphate ($PF_6^-$). The anionic species may alternatively be hydroxide, or an alkoxide (e.g., methoxide or ethoxide). The anionic species may alternatively be a carboxylate species, such as formate, acetate, propionate, or glycolate. In other embodiments, the anionic species ($X^{m-}$) can be an oxyanion. As used herein, the term "oxyanion" refers to an anion having at least three or four oxygen atoms, wherein the oxygen atoms are generally all bound to a central element. Some examples of oxyanions include sulfate (e.g., $SO_4^{2-}$), nitrate ($NO_3^-$), chromate (e.g., $CrO_4^{2-}$), selenate (e.g., $SeO_4^{2-}$), phosphate (e.g., $PO_4^{3-}$), arsenate ($AsO_4^{3-}$), carbonate ($CO_3^{2-}$), bicarbonate ($HCO_3^-$), and perchlorate ($ClO_4^-$). The oxyanions provided above may or may not also include related derivatives. For example, unless otherwise stated, the term "sulfate" may also include thiosulfate ($S_2O_3^{2-}$), bisulfate ($HSO_4^-$), and sulfite ($SO_3^{2-}$). Similarly, the term "chromate" may also include $Cr_2O_7^{2-}$ (dichromate). Similarly, the term "phosphate" may also include hydrogenphosphate ($HPO_4^{2-}$), dihydrogenphosphate ($H_2PO_4^-$), pyrophosphate ($P_2O_7^{4-}$), thiosphosphates (e.g., $PO_3S_3^{3-}$ or $PO_2S_2^{3-}$), and phosphite (e.g., $PO_3^{3-}$, $HPO_3^{2-}$, or $H_2PO_3^-$). The oxyanion may also be selected from among less common species, such as tungstate, vanadate, molybdate, tellurate, and stannate.

The ring-containing moiety (A) is or includes any cyclic group that includes at least one, two, three, or four carbon ring atoms. Since the cyclic group is attached to two iminoguanidine or iminoguanidinium groups, the cyclic group in the ring-containing moiety (A) necessarily includes two sites engaged in bonds, either directly, or indirectly via a linker, to the iminoguanidine or iminoguanidinium groups. Typically, the two sites in the ring (A) linked, directly or indirectly, to the iminoguanidine or iminoguanidinium groups are ring carbon atoms. In some embodiments, the ring-containing moiety is or includes a monocyclic ring, i.e., a single ring not bound or fused to another ring. In other embodiments, the ring-containing moiety is or includes a ring system, wherein the term "ring system" refers to a polycyclic moiety (e.g., a bicyclic or tricyclic moiety). The cyclic group can be polycyclic by either possessing a bond between at least two rings or a shared (i.e., fused) bond between at least two rings. The one or more rings in the ring-containing moiety is typically a five-membered, six-membered, or seven-membered ring.

In one set of embodiments, the ring-containing moiety (A) is or includes a carbocyclic ring or ring system. The term "carbocyclic" indicates that the ring or ring system contains only carbon ring atoms. The carbocyclic ring or ring system can be saturated or unsaturated. Some examples of carbocyclic rings that are monocyclic and saturated include cyclopentyl, cyclohexyl, and cycloheptyl rings. Some examples of carbocyclic rings that are monocyclic and unsaturated (which may be aliphatic or aromatic) include cyclopentenyl, cyclopentadienyl, cyclohexenyl, cyclohexadienyl, cycloheptenyl, cycloheptadienyl, and phenylene (benzene) rings. Some examples of carbocyclic rings that are polycyclic and saturated include decalin, norbornane, bicyclohexane, and 1,2-dicyclohexylethane ring systems. Some examples of carbocyclic rings that are polycyclic and unsaturated include naphthalene, anthracene, phenanthrene, phenalene, and indene ring systems.

In another set of embodiments, the ring-containing moiety (A) is or includes a heterocyclic ring or ring system. The term "heterocyclic" indicates that the ring or ring system contains at least one ring heteroatom. The ring heteroatom is typically selected from nitrogen, oxygen, and sulfur. The heterocyclic ring or ring system can be saturated or unsaturated. Some examples of heterocyclic saturated rings or ring systems include those containing at least one ring nitrogen atom (e.g., pyrrolidine, piperidine, piperazine, imidazolidine, azepane, and decahydroquinoline rings); those containing at least one ring oxygen atom (e.g., oxetane, tetrahydrofuran, tetrahydropyran, 1,4-dioxane, 1,3-dioxane, and 1,3-dioxepane rings); those containing at least one ring sulfur atom (e.g., tetrahydrothiophene, tetrahydrothiopyran, 1,4-dithiane, 1,3-dithiane, and 1,3-dithiolane rings); those containing at least one ring oxygen atom and at least one ring nitrogen atom (e.g., morpholine and oxazolidine rings); and those containing at least one ring nitrogen atom and at least one ring sulfur atom (e.g., thiazolidine and thiamorpholine rings). Some examples of heterocyclic unsaturated rings or ring systems include those containing at least one ring nitrogen atom (e.g., pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, and 1,8-naphthyridine rings); those containing at least one ring oxygen atom (e.g., furan, pyran, 1,4-dioxin, benzofuran, dibenzofuran, and dibenzodioxin); those containing at least one ring sulfur atom (e.g., thiophene, thianaphthene, benzothiophene, thiochroman, and thiochromene rings); those containing at least one ring oxygen atom and at least one ring nitrogen atom (e.g., oxazole, isoxazole, benzoxazole, benzisoxazole, oxazoline, 1,2,5-oxadiazole (furazan), and 1,3,4-oxadiazole rings); and those containing at least one ring nitrogen atom and at least one ring sulfur atom (e.g., thiazole, isothiazole, benzothiazole, benzoisothiazole, thiazoline, and 1,3,4-thiadiazole rings).

Some examples of compounds according to Formula (1a) include the following:

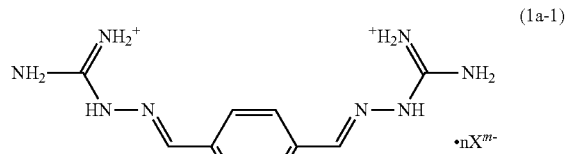

(1a-1)

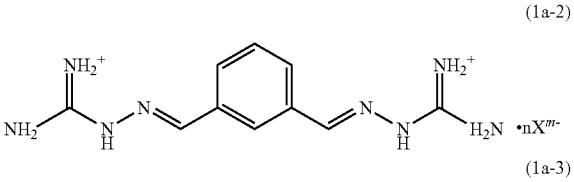

(1a-2)

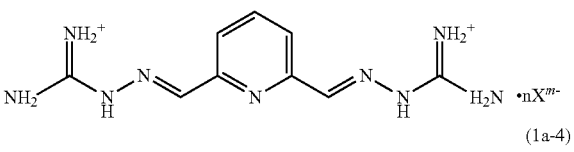

(1a-3)

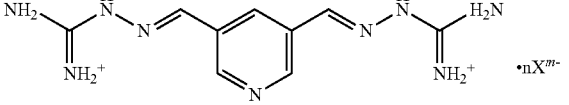

(1a-4)

-continued

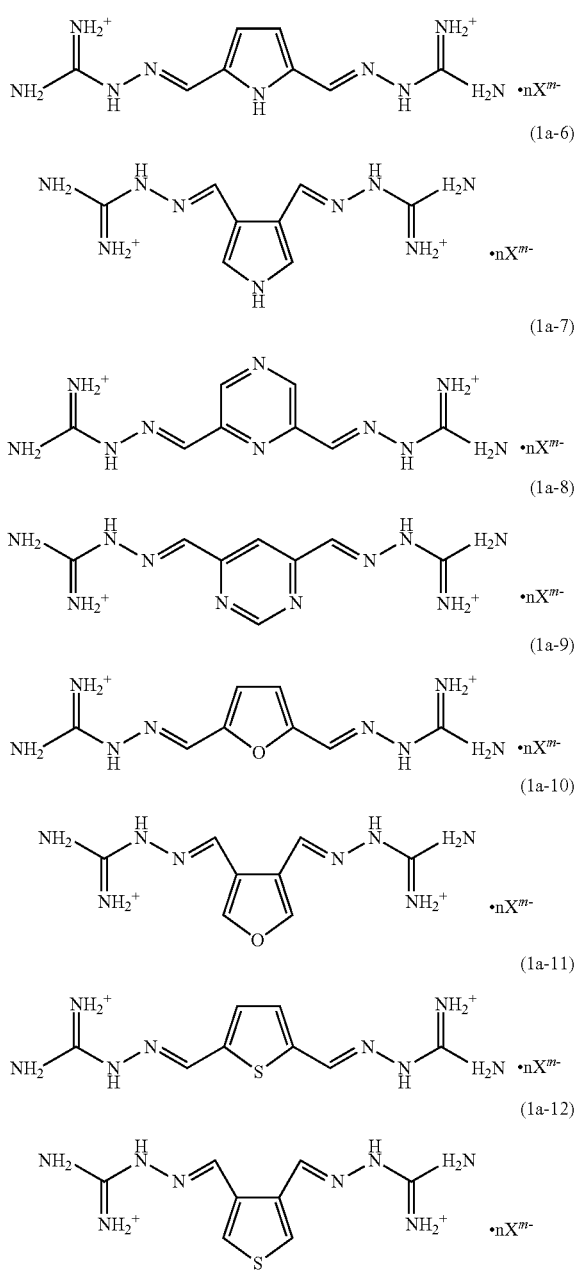

Any of the above exemplary compounds may also be converted to the respective neutral analogue according to Formula (1) by removal of the two protons located on positively charged amine groups. Moreover, in any of the above exemplary formulas, a hydrogen atom on a ring nitrogen atom may be replaced with a hydrocarbon group, such as a methyl, ethyl, n-propyl, isopropyl, in-butyl, isobutyl, sec-butyl, t-butyl, phenyl, or benzyl group. As also provided above, one or more of the hydrogen atoms in any of the above exemplary structures, whether the hydrogen atoms are shown or not shown, may be replaced with one or more methyl groups, respectively.

The compounds according to Formulas (1) and (1a) can be synthesized by methods well known in the art. In particular embodiments, the compounds according to Formulas (1) and (1a) are synthesized by reacting aminoguanidine or aminoguanidinium chloride (or a methylated derivative thereof) with a ring-containing dialdehyde or diketone under conditions where an imine linkage is formed between an amino group on the aminoguanidine or aminoguanidinium molecule and the carbon of the aldehyde or ketone group. The ring-containing dialdehyde or diketone includes a ring-containing moiety (A), as described above. A general schematic of the process is provided as follows:

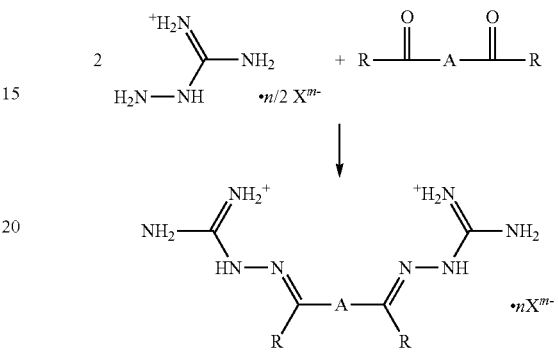

In the above scheme, A is a ring-containing moiety, as described above. The group R is typically hydrogen (which corresponds to a dialdehyde reactant), but R may be a hydrocarbon group, such as methyl, ethyl, n-propyl, isopropyl, n-butyl, isobutyl, sec-butyl, t-butyl, phenyl, or benzyl group, which corresponds to a diketone reactant. The above scheme is meant to be inclusive of producing a neutral bis-iminoguanidine compound according to Formula (1). To produce the neutral compound, aminoguanidine can be used in the above scheme instead of a guanidinium salt, or alternatively, the guanidinium salt can be produced and converted to the neutral guanidine compound by reaction with a base. Moreover, any one or more hydrogen atoms of the aminoguanidine or aminoguanidinium reactant may be replaced with one or more methyl groups, respectively, except that the aminoguanidine or aminoguanidinium reactant should retain at least one primary amine group for reaction with the dialdehyde or diketone. Alternatively, one or more hydrogen atoms of the bis-iminoguanidinium or bis-iminoguanidine product may be replaced with one or more methyl groups by, for example, reaction with methyl iodide.

In another aspect, the invention is directed to a method for removing one or more oxyanions from an aqueous source containing the oxyanion by contact of the aqueous source with any of the bis-iminoguanidinium compounds ("oxyanion precipitating compounds") of Formula (1a), as described above, wherein the anionic species ($X^{m-}$) in Formula (1a), before contact with the aqueous source, is exchangeable with the oxyanion to be removed from the aqueous source. In some embodiments, the anionic species in Formula (1a), before contact with the aqueous source, is more specifically a halide or pseudohalide. The oxyanion(s) in the aqueous source can be one or more of any of the oxyanions described above. The aqueous source can be any source containing one or more oxyanions to be removed. The oxyanion to be removed is generally present in the aqueous source as an inorganic salt that is dissolved or suspended in the aqueous source. In some cases, at least one of the oxyanions is in the form of an insoluble scale, such as $CaSO_4$, $SrSO_4$, or $BaSO_4$ scale. Scale is often a major problem in oil field injection operations and the method described herein offers a solution to scale removal. The aqueous medium is typically composed predominantly or completely of water, such as found in seawater, water from sewage treatment, or aqueous effluent from an industrial or commercial process. However, in some embodiments, the aqueous medium may include an organic solvent miscible in water, such as an alcohol, acetone, or the like.

In the method for removing one or more oxyanions from an aqueous source, the oxyanion precipitating compound is dissolved in the aqueous source. The foregoing dissolution process can be referred to as "step (i)". The oxyanion precipitating compound refers to any of the bis-iminoguanidinium compounds of Formula (1a) where the anionic species ($X^{m-}$) is exchangeable with the oxyanion to be removed from the aqueous source. That is, the anionic species ($X^{m-}$) in the bis-iminoguanidinium compound of Formula (1a), before being contacted with and dissolved into the aqueous source, should be capable of being replaced with the oxyanion to be removed from the aqueous source. For example, the bis-iminoguanidinium compound of Formula (1a) may take the anionic species ($X^{m-}$) as a halide or pseudohalide, before contact of the bis-iminoguanidinium compound of Formula (1a) with the aqueous source, in a situation where the oxyanion to be removed from the aqueous source is sulfate, nitrate, chromate, selenate, phosphate, arsenate, carbonate, bicarbonate, or perchlorate. The oxyanion precipitating compound can be dissolved by any suitable means, such as by directly adding solid oxyanion precipitating compound to the aqueous source or by adding a pre-made solution, suspension, or slurry of the oxyanion precipitating compound to the aqueous source.

The oxyanion precipitating compound is added to the aqueous source in such amount and under such conditions (e.g., temperature) that result in precipitation of an oxyanion salt of the oxyanion precipitating compound. For example, in the case where the oxyanion precipitating compound being added to the aqueous source corresponds to the bis-iminoguanidinium compound of Formula (1a) where the anionic species ($X^{m-}$) is halide or a pseudohalide, and the oxyanion to be removed from the aqueous source is sulfate, the oxyanion precipitating compound should be added to the aqueous source in sufficient amount and under appropriate conditions to result in replacement of the halide or pseudohalide with sulfate in the bis-iminoguanidinium compound of Formula (1a). The result is that the resulting precipitated salt corresponds to a salt of the bis-iminoguanidinium compound of Formula (1a) where the anionic species $X^{m-}$ is the oxyanion (e.g., sulfate) being removed from the aqueous source. Generally, the oxyanion precipitating compound is added to the aqueous source in an amount corresponding to at least, and generally above, the molar amount of oxyanion expected to be contained within a sample of aqueous source to be processed. The term "precipitation," as used herein, refers to the separation of the oxyanion salt, as a solid, from the aqueous source. The precipitate can be, for example, an amorphous solid (e.g., as scale, sludge, or powder) or crystalline material. In preferred embodiments, the precipitate is in crystalline form, since crystal formation functions as an additional driving force for removal of the oxyanion salt from solution.

Following the dissolution of the oxyanion precipitating compound of Formula (1a) and precipitation of the oxyanion salt of Formula (1a) in step (i), the precipitated oxyanion salt is removed from the aqueous source to result in water substantially reduced in the concentration of the oxyanion originally present in the aqueous source. The removal step can be referred to as step (ii). The precipitated oxyanion salt can be removed by any of the means well known in the art for removing solid material from a liquid. The precipitated oxyanion salt can be removed by, for example, filtration, or by centrifugation followed by decanting, or by a combination thereof. By use of the oxyanion precipitating compounds described herein, the oxyanion salt being removed can be reduced by at least or above 98%, 99%, 99.5%, or 99.9% compared to the original concentration of the oxyanion in the aqueous source.

In the process described above for removing one or more oxyanions from an aqueous source, the resulting precipitated oxyanion salt can be conveniently processed to regenerate the starting oxyanion precipitating compound according to Formula (1a). By regenerating the starting oxyanion precipitating compound, the process can advantageously include a recycling step, which makes the process further cost effective with minimal environmental impact. To regenerate the starting oxyanion precipitating compound, the precipitated oxyanion salt (e.g., Formula (1a) in which $X^{m-}$ is sulfate) can be reacted with a base (e.g., a metal hydroxide, organic amine, or ammonia) that converts the cationic form of the oxyanion precipitating compound (according to Formula (1a)) to the neutral form depicted in Formula (1) while at the same time forming a byproduct salt (e.g., metal sulfate, organoammonium sulfate, or ammonium sulfate, respectively) with the oxyanion originally bound with the oxyanion precipitating compound. The neutral compound depicted in Formula (1) is then reacted with a protic acid (e.g., HCl, HBr, or HNO$_3$, etc.) to produce the original cationic form according to Formula (1a) with $X^{m-}$ being the conjugate base of the acid used (e.g., Cl$^-$, Br$^-$, or NO$_3^-$, respectively).

In another aspect, the invention is directed to a method for removing carbon dioxide from a gaseous source by contacting the gaseous source with an aqueous solution containing a bis-iminoguanidinium compound of Formula (1a) wherein the anionic species ($X^{m-}$) is hydroxide. By virtue of the hydroxide anion in the bis-iminoguanidinium compound of Formula (1a), the bis-iminoguanidinium compound of Formula (1a) functions as a carbon dioxide complexing (capturing) compound. More specifically, the hydroxide anion in the bis-iminoguanidinium compound of Formula (1a) reacts with carbon dioxide to form a carbonate or bicarbonate anion. The resulting carbonate or bicarbonate anion associates with the bis-iminoguanidinium compound of Formula (1a) to form a carbonate or bicarbonate salt of the bis-iminoguanidinium compound of Formula (1a). The gaseous source can be any volume of gas containing carbon dioxide. The gaseous source can be, for example, air, waste gas from an industrial or commercial process, flue gas from a power plant, exhaust from an engine, or sewage or landfill gas.

In one embodiment, the bis-iminoguanidinium-hydroxide compound is prepared before it is dissolved in an aqueous medium to produce the aqueous solution. In another embodiment, the bis-iminoguanidinium-hydroxide compound is produced in the aqueous medium in situ by adding a neutral bis-iminoguanidine compound according to Formula (1) to the aqueous medium, in which case the neutral bis-iminoguanidine compound spontaneously reacts, via its substantial alkalinity, with water molecules to form a bis-iminoguanidinium according to Formula (1a) in which the anionic species is hydroxide.

In the carbon dioxide removal process, the gaseous source is contacted with the aqueous solution containing the carbon dioxide complexing compound by any means that permits the gaseous source to dissolve into the aqueous solution. The gaseous source can, for example, be bubbled through the aqueous solution, with or without agitation of the aqueous solution. Alternatively, the gaseous source may be sprayed or misted with the aqueous solution, which may be performed in the presence of a layer of the aqueous solution under agitation to further absorb the carbon dioxide. When the carbon dioxide complexing compound contacts the dissolved carbon dioxide, the hydroxide anion in the carbon dioxide complexing compound reacts with the carbon dioxide so as to form a carbonate or bicarbonate salt of the carbon dioxide complexing compound, i.e., a carbonate or bicarbonate salt of the bis-iminoguanidinium compound of Formula (1a). The carbonate or bicarbonate salt of the bis-iminoguanidinium compound of Formula (1a) precipitates from the aqueous solution, either as amorphous powder form or in crystalline form, as described above in the oxyanion removal process. The foregoing contacting and precipitating stage may be referred to as step (i).

After the carbonate or bicarbonate salt of the bis-iminoguanidinium compound of Formula (1a) is precipitated, the precipitate is removed from the aqueous solution by any suitable means, such as filtration, as described above for the oxyanion removal process. The foregoing removal step may be referred to as step (ii). Moreover, the resulting carbonate or bicarbonate salt can be processed, such as by heating, to recover the starting bis-iminoguanidinium-hydroxide within the scope of Formula (1a) or the starting neutral bis-iminoguanidine compound within the scope of Formula (1) with simultaneous evolution of carbon dioxide gas. The evolved carbon dioxide gas may be stored and/or pressurized, as appropriate, and may be subsequently further processed or reacted in an industrial or commercial process.

In the above-described process for capturing carbon dioxide, the bis-iminoguanidinium compound according to Formula (1a) captures the carbon dioxide directly by converting carbon dioxide to carbonate or bicarbonate and forming a salt with the carbonate or bicarbonate. However, in some embodiments, the carbon dioxide to carbonate conversion process can be separated from the salt formation process. A separated process can be particularly advantageous when using a $CO_2$ sorbent that can capture and convert the carbon dioxide to carbonate significantly faster than the bis-iminoguanidinium-hydroxide compound in Formula (1a). In this way, a highly efficient $CO_2$ sorbent can quickly capture and convert carbon dioxide to carbonate, and a bis-iminoguanidinium compound according to Formula (1a) can quickly form an insoluble salt with the carbonate, thereby removing the carbon dioxide in a more efficient manner. In the two-part process, the anion of the bis-iminoguanidinium can be any anion that can be replaced with carbonate or bicarbonate, such as hydroxide or a halide. The $CO_2$ sorbent is typically an aqueous solution in which a base reactive with carbon dioxide is included. The base may be, for example, a metal hydroxide (e.g., NaOH or KOH), alkali carbonate, or an amine-containing molecule other than those described in Formulas (1) and (1a), e.g., methylamine, ethylamine, ethylenediamine, ethanolamine, and amino acids (e.g., glycine, sarcosine, taurine, alanine, valine, leucine, serine, threonine, glutamine, asparagine, lysine, arginine, and phenylalanine).

Examples have been set forth below for the purpose of illustration and to describe certain specific embodiments of the invention. However, the scope of this invention is not to be in any way limited by the examples set forth herein.

EXAMPLES

Synthesis of 1,4-benzene-bis(iminoguanidinium) (BBIG) Compounds

The synthetic process used in preparing the BBIG compounds is summarized by the following scheme:

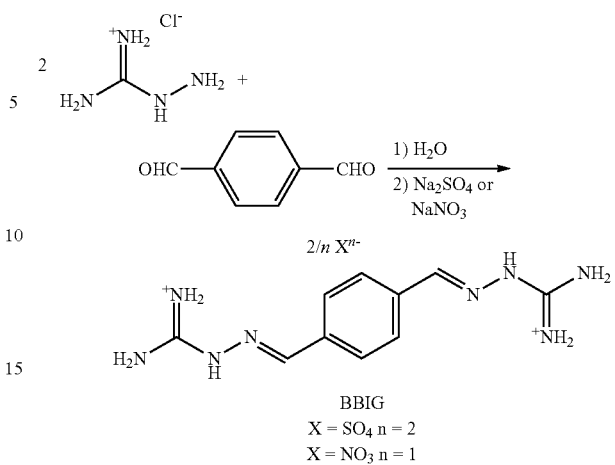

In brief, aqueous condensation of aminoguanidinium chloride with terephthalaldehyde led to the in situ formation of the 1,4-benzene-bis(iminoguanidinium) cation (BBIG), which crystallized as the sulfate (BBIG-$SO_4$) or nitrate (BBIG-$NO_3$) salt in the presence of $Na_2SO_4$ or $NaNO_3$, respectively.

Preparation of BBIG-Cl (1)

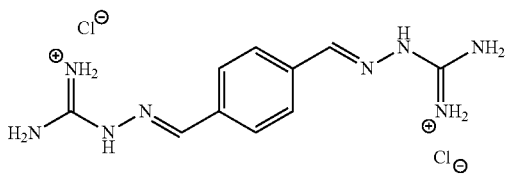

4 grams of terephthalaldehyde and 7.26 grams of aminoguanidinium chloride were added to 20 mL of ethanol in a 50 mL round bottom flask equipped with a magnetic stir bar. The solution was heated to 60° C. using a hotplate, and stirred with a magnetic stir bar for 2 hours. The solution was cooled to 20° C. and allowed to sit for three hours, before collecting the solid by vacuum filtration through a filter-paper equipped Buchner funnel. The obtained solid was suspended in 20 mL of ethanol and the suspension heated on a hotplate until boiling. If the solid did not go completely into solution at this point, one or more small aliquots (1 mL) of ethanol were added, followed by bringing the solution to boiling until all solid became dissolved. The flask was allowed to cool to room temperature, then placed in a 0° C. freezer overnight. The solid was collected by filtering through a filter-paper equipped Buchner funnel using vacuum filtration.

Preparation of BBIG-$SO_4$

A mixture of solid terephthalaldehyde (0.5 mmol, 0.067 g), aqueous aminoguanidinium chloride (1.1 mmol, 2.2 mL, 0.5 M), and water (10 mL) was stirred magnetically for 4 hours, which resulted in a slightly yellow solution. Addition of sodium sulfate (0.5 mmol, 0.5 mL, 1 M) to this solution resulted in instant precipitation of a crystalline white solid. The crystalline solid was filtered after two weeks and washed with water. Yield: 0.164 g (86%). HRMS (ESI-MS): m/z calcd for $C_{10}H_{15}N_8^+$: 247.14140; found: 247.14100; elemental analysis calcd (%) for $C_{10}H_{20}N_8O_6S$: C; 31.58, H; 5.30, N; 29.46; found: C; 31.61, H; 5.53, N; 29.04. X-ray quality single crystals were obtained by slow evaporation of a solution containing aminoguanidinium chloride, terephthalaldehyde, and tetrabutylammonium sulfate in water/DMF. The simulated powder pattern from the single-crystal X-ray structural analysis matched the experimental PXRD pattern of bulk $BBIG-SO_4$ precipitated from water.

Preparation of $BBIG-NO_3$: A mixture of solid terephthalaldehyde (0.5 mmol, 0.067 g), aqueous aminoguanidinium chloride (1.5 mmol, 3 mL, 0.5 M), and water (10 mL) was stirred magnetically for 5 hours, which resulted in a slightly yellow solution. Addition of sodium nitrate (1 mmol, 1 mL, 1 M) to this solution resulted in precipitation of a crystalline white solid after about 10 minutes. The mixture was stirred for 12 hours, before the crystalline solid was filtered and washed with water and ethanol. Yield 0.150 g (81%). HRMS (ESI-MS): m/z calcd for $C_{10}H_{15}N_8^+$: 247.14140; found: 247.14130; elemental analysis calcd (%) for $C_{10}H_6N_{10}O_6$: C; 32.26, H; 4.33, N; 37.62; found: C; 32.57, H; 4.50, N; 6.64. X-ray quality single crystals were obtained by leaving the mixture containing the initially precipitated solid undisturbed for two weeks. The simulated powder pattern from the single-crystal X-ray structural analysis matched the experimental PXRD pattern of bulk $BBIG-NO_3$ precipitated from water.

Synthesis of 2,6-pyridine-bis(iminoguanidine) (PyBIG)

2,6-pyridine-bis(iminoguanidine) (PyBIG) was obtained by imine condensation of 2,6-pyridinedialdehyde with aminoguanidinium chloride, followed by neutralization with aqueous NaOH, which led to precipitation of the pure compound as a crystalline hydrate ($PyBIG.2.5H_2O$). The details of the synthesis are as follows:

Pyridine-2,6-dicarbaldehyde

A mixture of pyridine-2,6-dimethanol (10.00 g, 71.86 mmol) and Dess-Martin periodinane (67.06 g, 158.10 mmol) were suspended in 400 mL of dichloromethane. The reaction mixture was stirred at room temperature for 12 hours. Subsequently, 100 mL of water was added to the reaction and the mixture was stirred at room temperature for an additional 12 hours. A 300 mL 50/50 mixture of saturated $NaHCO_3$ and 10% $Na_2S_2O_3$ was added to the reaction mixture and stirred for two additional hours, then the mixture was filtered through a celite plug. The filtrate was poured into a separatory funnel and the organic layer was collected, washed with brine, and dried with $Na_2SO_4$. The dichloromethane was removed under vacuum resulting in a white-yellow solid. The product was purified by column chromatography using the following methodology. The solid was partly dissolved in hexanes and loaded onto a silica gel column (Note: the solid is not fully soluble in hexanes), and eluted using a hexanes-ethyl acetate solvent system (7:3 hexanes/ethyl acetate). The final product was isolated as a white solid. Yield: 7.64 g, 78.7%. $_1$H NMR (400 MHz, $CDCl_3$) δ 10.136 (2H, s), 8.164 (2H, d), 8.070 (1H, t). $^{13}$C NMR (100 MHz, CDCl3) δ 192.38, 152.99, 138.43, 125.36.

PyBIG.2HCl (2)

Pyridine-2,6-dicarbaldehyde (7.64 g, 56.54 mmol) was suspended in 200 mL of absolute ethanol, then aminoguanidinium chloride (13.75 g, 124.37 mmol) was added to the suspension. The reaction mixture was mechanically stirred and heated to 65° C. for 8 hours (Note: as the reaction progresses, small amounts of the aldehyde dissolves and the bis-iminoguanidinium product precipitates out of solution as a white solid). After 8 hours, the product (PyBIG.2HCl) was obtained as a white solid by vacuum filtration of the reaction mixture, and washed with diethyl ether to remove unreacted pyridine-2,6-dicarbaldehyde. Yield: 90.8%. $^1$H NMR (400 MHz, $D_2O$) δ 7.779 (1H, t), 7.717 (2H, s), 7.681 (2H, d). $^{13}$C NMR (100 MHz, $D_2O$) δ 154.96, 150.99, 145.20, 138.75, 123.51. The foregoing product has the following structure:

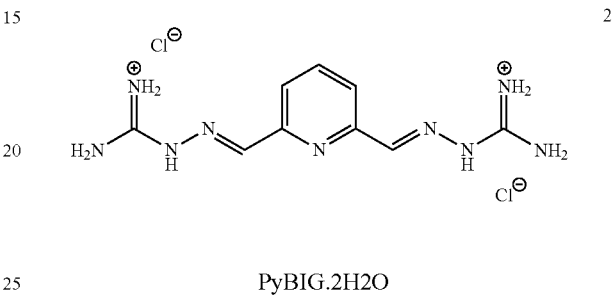

PyBIG.2H2O

PyBIG-2HCl (10.00 g, 31.23 mmol) was dissolved in 350 mL of water and the mixture was stirred for 1 hour to ensure complete dissolution of the chloride salt. Subsequently, NaOH (6.9 mL, 10 M) was added, resulting in immediate precipitation of the free compound. The suspension was stirred for 4 hours, and then the pure PyBIG.2H2O compound was isolated as an off-white solid by vacuum filtration and drying under vacuum at room temperature overnight. Yield: 96.1% (7.72 g). $^1$H NMR (400 MHz, DMSO-$d_6$) δ 7.999 (2H, s), 7.915 (2H, d), 7.647 (1H, t) 6.145 (4H, s) 5.924 (4H, s). $^{13}$C NMR (100 MHz, DMSO-$d_6$) δ 161.91, 155.65, 143.88, 136.29, 118.19.

Solubility Measurements of BBIG-Cl, $BBIG-SO_4$, and $BBIG-NO_3$

The solubility of BBIG-Cl was determined gravimetrically. A saturated solution of BBIG-Cl was obtained by placing an excess of the salt in a 15 mL polypropylene centrifuge tube and adding 2 mL of deionized water (milliQ). The resulting suspension was mixed for 48 hours using a rugged rotator set at 60 rpm, inside an incubator set at 258° C. After 48 hours, the suspension was centrifuged for 10 minutes at 3000 rpm to separate the aqueous and solid phases. The aqueous layer was then carefully removed using a 0.22 μm syringe filter to remove any remaining suspended solid from the solution. One mL of the saturated salt solution was then pipetted into a pre-weighed glass vial containing a magnetic stir bar. The water was then removed under reduced pressure and gentle heating (~50° C.) while stirring. The resulting solid was left under vacuum overnight to ensure complete removal of the water, prior to weighing the vial. The solubility measurements were run in triplicate, and the average weight of the recovered chloride salt was 0.0202 g, which corresponds to an aqueous solubility of 6.3(±0.2)× 10.2 M.

The solubilities of BBIG-SO4 and BBIG-NO3 were determined by UV spectroscopy. Prior to determining the solubility of these salts, a calibration curve was obtained using the more soluble BBIG-Cl salt. Saturated solutions of the $BBIG-SO_4$ and $BBIG-NO_3$ salts were prepared the same way as for BBIG-Cl. These solutions were then diluted to ensure the concentrations of the BBIG di-cation were in the concentration range of the calibration curve. The BBIG-$NO_3$ solutions were diluted 100-fold, whereas the BBIG-$SO_4$ solutions were diluted tenfold. The solubilities were then determined from the UV spectra of these diluted solutions by measurement of the absorbance maxima at 322 nm and comparison with the calibration curve. The solubility measurements were run in triplicate, and the obtained averages and standard deviations for BBIG-$SO_4$ and BBIG-$NO_3$ were $1.6(2) \times 10^{-5}$ M and $6.5(5) \times 10^{-4}$ M, respectively.

Variable-Temperature Solubility Measurements of BBIG-$SO_4$

All measurements were done in triplicate and the reported solubilities are the average values. Excess amounts of BBIG-$SO_4$ were mixed with 10 mL of MilliQ water in 15 mL polypropylene centrifuge tubes. The resulting suspensions were mixed for 72 hours using a rugged rotator set at 60 rpm, inside an incubator set at 15, 20, 25, 30, or 35° C. Subsequently, the samples were removed and centrifuged for 10 minutes at 3000 rpm to separate the aqueous and solid phases. A 3 mL aliquot was then removed from each sample for UV analysis. Then 3 mL of fresh MilliQ water was added to the samples to replace the aliquot of solution removed, and the samples were mixed for an additional 72 hours at the next desired temperature before further sub-sampling. The temperatures were maintained by using temperature controlled incubators containing NIST certified thermometers. The 3 mL aliquots of subsampled solutions were filtered through a 0.22 μm syringe filter to ensure any suspended solid was removed from the solutions prior to diluting the samples using the same dilution factors used in determining the solubilities at 258° C., as described above. The solubilities were determined by UV spectrometry, as described in the previous section.

Competitive Crystallization of BBIG-$SO_4$ from an Aqueous Mixture of Sulfate, Nitrate, and Chloride First, BBIG-Cl was generated in situ from terephthalaldehyde and aminoguanidinium chloride, as follows. Terephthalaldehyde (0.5 mmol, 0.067 g), aminoguanidinium chloride (1.5 mmol, 3 mL, 0.5 M) and water (10 mL) were added to a 20 mL vial. The mixture was stirred at room temperature for 5 hours, which resulted in dissolution of most of the suspended solid. A few drops of 1M HCl were then added to adjust the pH to around 5, which resulted in a clear, slightly yellow solution. Aqueous sodium sulfate (0.5 mmol, 0.5 mL, 1 M) and sodium nitrate (1 mmol, 1 mL, 1 M) were then added, which resulted in the formation of a white precipitate after about 2 minutes. The mixture was stirred at room temperature for 12 hours, before the crystalline solid was filtered and washed with water. Yield: 0.190 g (100%). PXRD and FT-IR analyses confirmed the crystallized solid was pure BBIG-$SO_4$.

Recovery of the BBIG Compound

BBIG-$SO_4$ (53.1 mg, 0.14 mmol) was added to a 2 mL solution of NaOH (10%) and the mixture was stirred for 2 hours at room temperature, which resulted in the formation of a yellow precipitate. The solid was filtered using a pre-weighed filter paper, rinsed with 200 mL of water, then dried under vacuum. Yield: 31.8 mg (93%) as yellow powder. $^1$H NMR (400 MHz, $CD_3OD$): δ=7.660 (s, 4H; CH), 8.015 ppm (s, 2H; N=CH). Dissolution of the yellow powder in 1 M HCl resulted in a clear solution of BBIG-Cl, which could be reused for sulfate separation, as demonstrated by precipitation of BBIG$SO_4$ upon addition of aqueous sodium sulfate. X-ray quality single crystals of BBIG·$2H_2O$ were obtained by slow evaporation of a solution containing a small amount of the recovered yellow powder dissolved into aqueous ethanol.

Sulfate Separation from Seawater

The seawater used in the experiment was collected from the gulf stream in the Atlantic Ocean. Prior to use, the water was pre-filtered to remove suspended particulates and small organisms. After filtration, 10 mL of the ocean water was spiked with 96 mL of the $^{35}$S radiotracer (as $Na_2^{35}SO_4$) for β liquid scintillation counting. The sulfate concentration in seawater was estimated to be about 30 mM by titration with $BaCl_2$. Stock solutions of BBIG-Cl in MilliQ water were prepared, with concentrations of 15, 30, 33, 45, and 60 mM. A volume of 0.75 mL of each of these solutions was pipetted into a 2 mL Eppendorf microcentrifuge tube, and 0.75 mL of seawater pre-spiked with the $^{35}$S radiotracer was added. The resulting solution mixtures were mixed for 24 hours using a rotating wheel set at 60 rpm in a temperature-controlled air-box set at 25±0.2° C. The tubes were then centrifuged for 10 minutes at 3000 rpm to separate the aqueous and solid phases, and 1 mL aliquot solutions were removed using 0.22 μm syringe filters for β liquid scintillation counting.

Analysis of Sulfate Concentration by β Liquid Scintillation Counting

The radiolabeled $^{35}$S radiotracer is a β emitter, thereby allowing determination of the sulfate concentration of a solution spiked with a known amount of $Na_2^{35}SO_4$ by β liquid scintillation counting. The seawater solutions were pre-spiked with 96 mL of the $^{35}$S radiotracer, as above. The amount of radiotracer used was based on the need to ensure approximately 4.5 to 5 million initial counts per minute (CMP)/mL of solution (Ci $mL^{-1}$). The volume of the spike solution was determined by factoring in the original activity of the solution and correcting for the short half-life of the $^{35}$S radiotracer. The $Na_2^{35}SO_4$ solution had completed 3.8 half-lives before use in this experiment. The 1 mL aliquot solutions removed from seawater (see above) were pipetted into 20 mL of Ultima Gold scintillation cocktail (PerkinElmer). It was necessary to use 20 mL of the cocktail to ensure complete solubility of the seawater solutions in the cocktail. The resulting mixtures were vigorously shaken to allow for complete dissolution and dispersion of the salt solutions. The samples were then placed on the analyzer and counted for 30 minutes after allowing 60 minutes for dark-adaption.

Results and Discussion

Figure 1B:
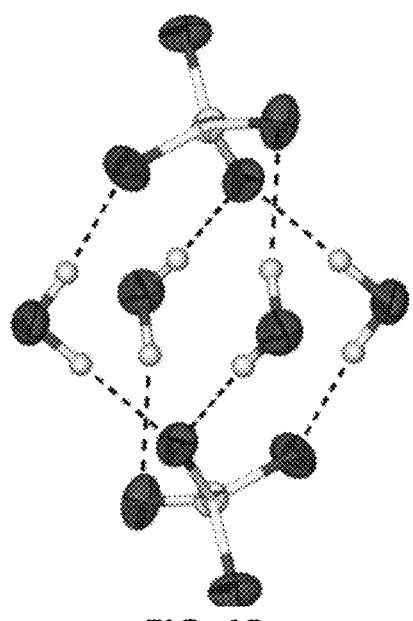
Figure 1C:
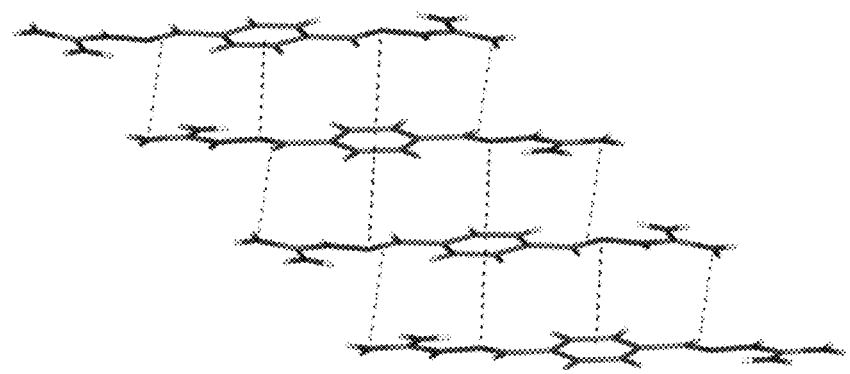
Figure 1D:
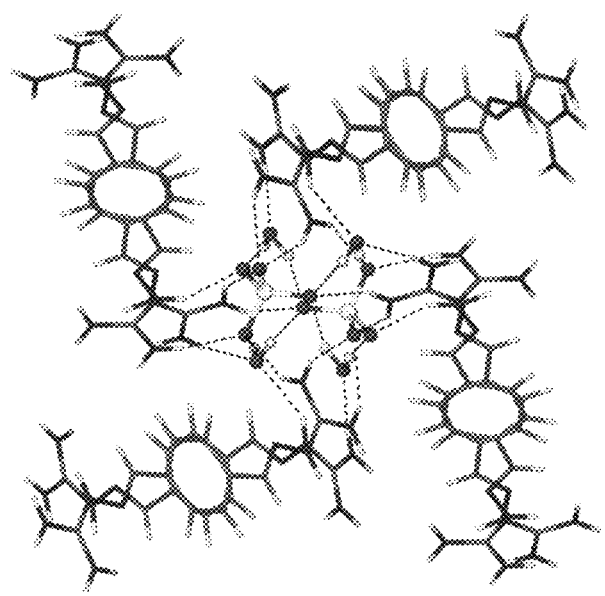

FIG. 1A shows the single-crystal X-ray structural of BBIG-$SO_4$. As shown in FIG. 1A, BBIG-$SO_4$ has a virtually planar conformation for the bis(iminoguanidinium) cation, and includes two water molecules of hydration in the crystal. As shown in the crystal structure perspective in FIG. 1B, pairs of sulfate anions are linked together by four water molecules into centrosymmetric $[(SO_4)_2(H_2O)_4]^{4-}$ clusters. Each sulfate anion in the cluster accepts four water hydrogen bonds, with observed OH . . . O contact distances of 1.82, 1.84, 1.88, and 2.20 Å, and OH—O angles of 169.8, 174.2, 156.6, and 167.38°, respectively. There are two crystallographically distinct BBIG cations in the crystal; one is perfectly planar, whereas the other is slightly bent, with its terminal $NH_2$ groups deviating by 0.2 Å out of the mean plane of the cation. As shown in the crystal structure perspective in FIG. 1C, the two cations are stacked in an antiparallel fashion in an ABAB pattern in the crystal, with a mean interplanar distance of 3.39 Å. The shortest intermolecular contacts between adjacent cations in the stacks are shown in inner and outer dashed lines in FIG. 1C, corresponding to contacts between the imine N atoms and the centroids of the benzene rings (3.35, 3.48 Å), and between terminal $NH_2$ groups and the centers of the C=N imine bonds (3.19, 3.33 Å), respectively. As shown by the more expansive crystal structure in FIG. 1D, the anionic $[(SO_4)_2(H_2O)_4]^{4-}$ clusters in the crystal are flanked by four cationic BBIG stacks, accepting a total of 20 NH . . . O hydrogen bonds from the guanidinium groups, of which 14 are to the sulfate anions, and 6 to the water molecules in the cluster. Thus, the total coordination number of each sulfate anion is 11, consisting of 7 NH . . . O hydrogen bonds from guanidinium groups, and 4 OH . . . O hydrogen bonds from water.

Figure 2A:
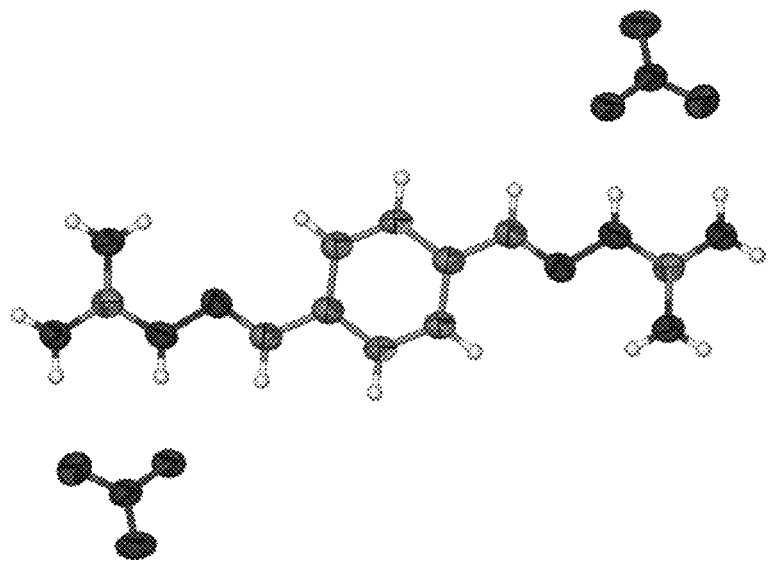
FIGS. 2A-2C. X-ray crystal structure views of 1,4-benzene-bis(iminoguanidinium) nitrate salt (BBIG-NO$_3$).
Figure 2B:
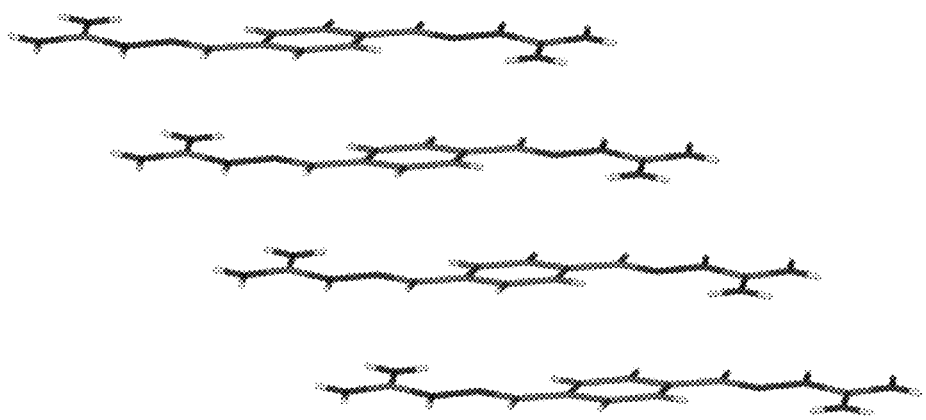
Figure 2C:
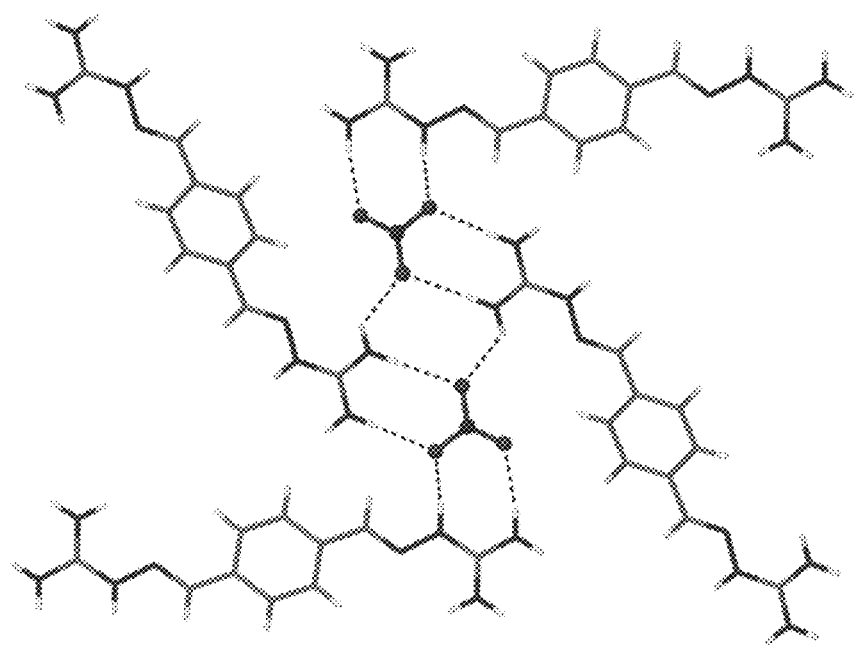

The X-ray crystal structure of $BBIG-NO_3$ is shown in FIG. 2A, with the stacking arrangement perspective shown in FIG. 2B. As in the analogous sulfate structure, the BBIG cations are stacked within the crystal, although in this case they are oriented parallel to each other, with a mean interplanar distance of 3.27 Å between adjacent cations in the stack. As shown in the more expansive view of FIG. 2C, the nitrate anions link the stacks into a three-dimensional hydrogen-bonded network, with each anion accepting five hydrogen bonds from three neighboring guanidinium groups.

Effective aqueous anion separation by crystallization of guanidines requires in the first place that the guanidinium salt of the targeted anion is relatively insoluble in water. For the crystallization to be selective, the guanidinium salt of the targeted anion also needs to be significantly less soluble than the corresponding salts of the competing anions. Table 1, below, lists the measured aqueous solubilities of the sulfate, nitrate, and chloride salts of BBIG.

TABLE 1

Aqueous solubilities of different BBIG salts at 25° C.

| BBIG Salt | Solubility (M) |
| --- | --- |
| sulfate[a] | $1.6(2) \times 10^{-5}$ |
| nitrate[a] | $6.5(5) \times 10^{-4}$ |
| chloride[b] | $6.3(2) \times 10^{-2}$ |

[a]Measured by UV spectroscopy,
[b]Measured gravimetrically

Figure 3:
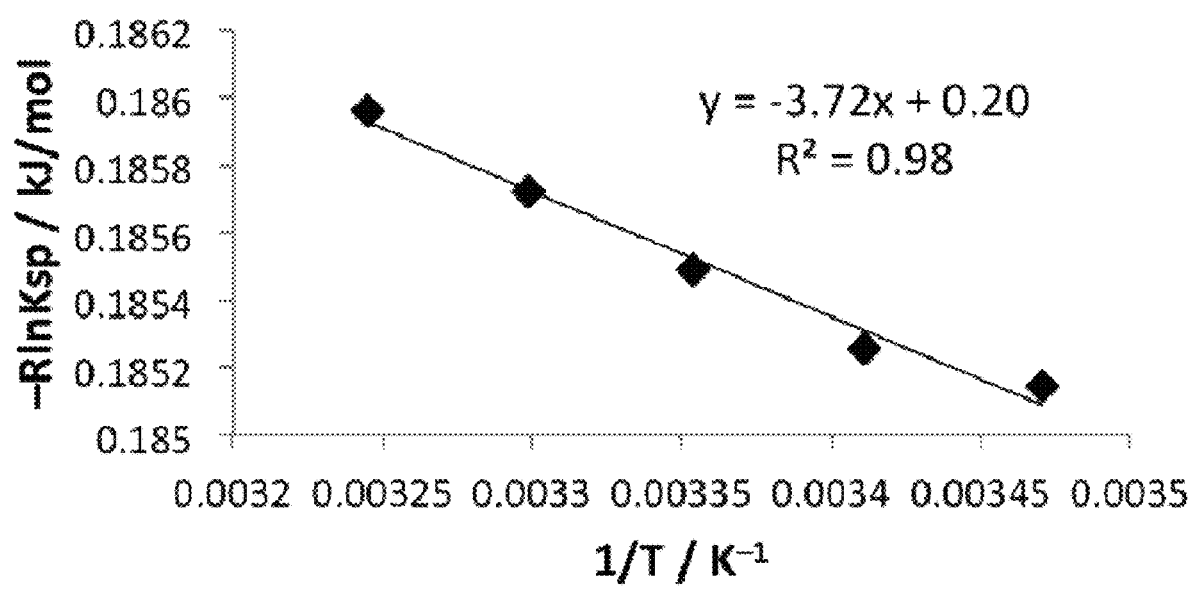
FIG. 3. Van't Hoff plot for dissolution of BBIG-SO$_4$ in the 15-358° C. temperature range.

The aqueous solubility of the sulfate salt was found to be lower than the corresponding solubilities of the nitrate and chloride analogues, by a factor of about 40 and 4000, respectively. Notably, the solubility of $BBIG-SO_4$ is also lower by a factor of 45 than the solubility of the glyoxal-bis-(iminoguanidinium) sulfate salt, as previously reported (R. Custelcean, et al., Angew. Chem. Int. Ed. 2015, 54, 10525; Angew. Chem. 2015, 127, 10671). The corresponding solubility product ($K_{sp}$) of $BBIG-SO_4$ is $2.4(\pm 0.6) \times 10^{-10}$, which is only marginally higher than the $K_s$ of $BaSO_4$ ($1.1 \times 10^{-10}$). Variable-temperature dissolution measurements indicated that the solubility of $BBIG-SO_4$ slightly decreases with increasing temperatures. From the van't Hoff plot shown in FIG. 3, it can be seen that the enthalpy of dissolution, as obtained from the slope of the plot, is $-3.7(\pm 0.8) \times 10^{-10}$ $kJmol^{-1}$. Thus, crystallization of $BBIG-SO_4$ is slightly endothermic and entropy driven. The exceptionally low aqueous solubility of $BBIG-SO_4$ is quite unusual for a guanidinium sulfate salt. This low solubility implies high stability for the $BBIG-SO_4$ crystals.

Electronic-structure calculations using density functional theory (DFT) indicated the stacking interactions between the bis-iminoguanidinium cations in the $BBIG-SO_4$ crystals are mainly electrostatic in nature. The electrostatic potential maps of the BBIG cation, either in the $BBIG-SO_4$ crystal, or isolated in the gas phase, showed that the C atoms, including those of the phenyl ring, tend to be electropositive, whereas the N atoms of the guanidinium and imine groups are all electronegative. The atomic charges of the BBIG cation were calculated using the Bader scheme. These charges are generally consistent with the relative offset of the BBIG cations observed in the $BBIG-SO4$ crystals (FIG. 1C), so that the closest intercationic contacts are between the terminal N atoms of the guanidinium groups (−1.31 charge) and the C atoms of the imine groups (+0.77 charge), and between the imine N atoms (−0.75 charge) and the C atoms of the Ph ring (+0.21, +0.13 charges). It thus appears that the stacking of the BBIG cations in these crystals is determined to a large extent by complementary electrostatic attractions between positive and negative regions of the planar cations.

Figure 4:
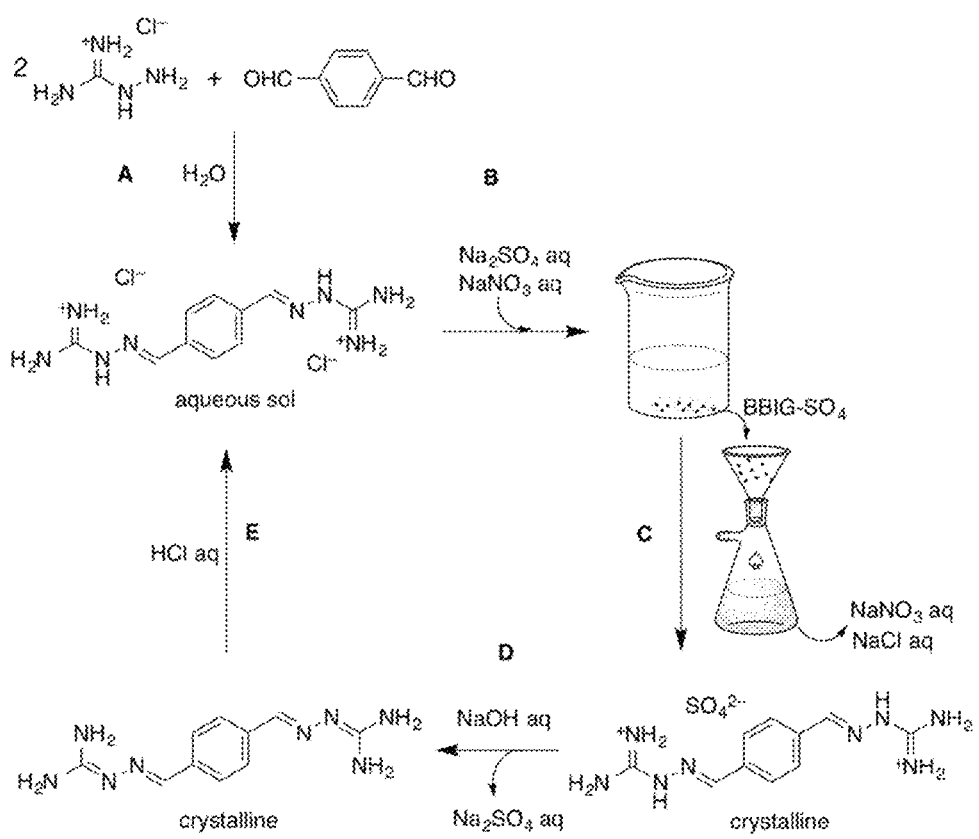
FIG. 4. Schematic diagram showing a complete separation cycle for sulfate removal by crystallization of BBIG-SO$_4$. Step A: In situ synthesis of BBIG dichloride salt from aqueous aminoguanidinium chloride and terephthaldehyde; Step B: Selective crystallization of BBIG-SO$_4$; Step C: Filtration of BBIG-SO$_4$; Step D: Compound recovery by neutralization of BBIG-SO$_4$ with NaOH and crystallization of neutral BBIG; sulfate is removed as aqueous Na$_2$SO$_4$; Step E: Regeneration of the BBIG dichloride salt, which can be recycled for another separation cycle.

Consistent with the measured aqueous solubilities that showed the sulfate salt was the least soluble in the series, crystallization of $BBIG-SO_4$ from an aqueous mixture containing chloride (0.1M), nitrate (0.07M), and sulfate (0.034M) proved highly selective, resulting in exclusive separation of the sulfate anion in quantitative yield. The BBIG compound was easily recovered by deprotonation of the guanidinium groups with 10% aqueous NaOH, which resulted in crystallization of the neutral BBIG compound in 93% yield. The compound can be recycled by converting it back into the cationic form with aqueous HCl. The overall sulfate separation cycle is provided in FIG. 4.

To demonstrate the real-world utility of this sulfate separation method, the removal of sulfate from seawater by selective crystallization of $BBIG-SO_4$ was attempted. The presence of relatively high concentrations of sulfate in seawater (~30 mM) poses significant scale problems in oil field injection operations. Once formed, the sulfate scale deposits (as $CaSO_4$, $SrSO_4$, and $BaSO_4$) are difficult to remove and cause major operational problems with high remedial costs, and in some cases, result in irreversible damage and well shutdown. It is, therefore, highly desirable to prevent the scale problems by removing sulfate from seawater.

Table 2, below, shows the results from the sulfate separation from seawater by crystallization of $BBIG-SO_4$. The sulfate concentration in solution was monitored by using radiolabeled $Na_2^{35}SO_4$ and β liquid scintillation counting, an analytical method typically used in liquid-liquid extractions, and recently demonstrated to also be effective in crystallization-based sulfate separations (R. Custelcean, et al., Cryst. Growth Des. 2015, 15, 517). Crystallization of $BBIG-SO_4$ from seawater proved very efficient, with 99% of sulfate being removed by using only 1.5 molar equivalents of the BBIG cation.

TABLE 2

Sulfate separation from seawater[a]

| BBIG [equiv][b] | $[SO_4^{2-}]$ left $[mM]$[c] | Amount of $SO_4^{2-}$ removed [%] |
| --- | --- | --- |
| 1 | 3.5 | 88 |
| 1.1 | 1.6 | 95 |
| 1.5 | 0.3 | 99 |
| 2 | 0.3 | 99 |

[a]Seawater from the Gulf Stream; the initial sulfate concentration was estimated at 30 mm by titration with $BaCl_2$;
[b]Molar equivalents of the BBIG dichloride salt added relative to the sulfate in seawater.
[c]Corresponding sulfate concentration left in the seawater, measured by using radiolabeled $Na_2^{35}SO_4$ and β liquid scintillation counting The above experimental results demonstrate an effective approach to aqueous sulfate separation by selective crystallization using an imine-linked bis-guanidinium compound self-assembled in situ from simple building blocks. The high sulfate crystallization efficiency stems from the exceptionally low aqueous solubility of the BBIG-SO$_4$ salt, which is significantly lower than the aqueous solubility of most, if not all, known organic sulfate salts, and comparable to that of BaSO$_4$. Furthermore, compared to precipitation with BaCl$_2$, the crystallization-based approach described here offers a greener alternative to aqueous sulfate separation that circumvents the use of toxic barium.

An important factor in the stability of the BBIG-SO$_4$ crystals appears to be the favorable stacking of the rigid and planar bis-iminoguanidinium cations, which are arranged to optimize the electrostatic attraction between the positive and negative areas of the cationic compounds. Another structural factor likely to play a key role in the low solubility of the BBIG-SO$_4$ crystals and the high sulfate crystallization selectivity is the sequestration of the sulfate anions as $[(SO_4)_2(H_2O)_4]^{4-}$ clusters and their complementary hydrogen bonding by the guanidinium groups. However, ultimately, the BBIG-SO$_4$ crystallization is entropy driven, presumably reflecting the entropically favorable release of water molecules from the strongly hydrated sulfate anions and the planar BBIG cations. Thus, this example of selective sulfate crystallization as sulfate-water clusters represents a complex recognition phenomenon that extends far beyond the simple lock-and-key principle commonly invoked in supramolecular chemistry. The selective crystallization involves a multitude of factors, including the mutual recognition of molecular and ionic components, a fine interplay of enthalpy and entropy, and a series of binding, self-assembly, and solvent exchange events that lead in the end to the nucleation and growth of highly insoluble crystals.

Compounds (1) and (2), in particular, exhibit very high degrees of separation of sulfate from seawater. The results are shown in Table 3, below.

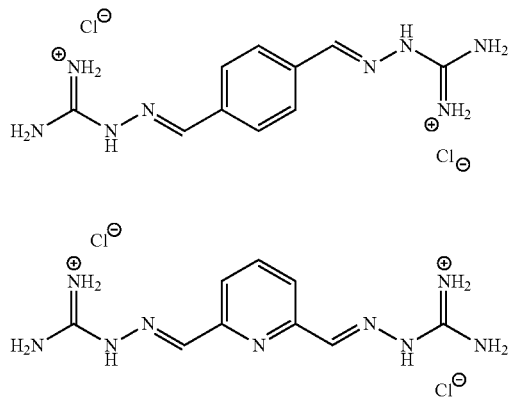

TABLE 3

| Sulfate removal abilities of Compounds 1 and 2 | | | |
|---|---|---|---|
| Initial Sulfate (mmol/L) | 1 (mmol/L) | % Sulfate Removed | Sulfate Left (mg/L) |
| 30 | 15 | 40.8 | 1706 |
| 30 | 15 | 41.8 | 1676 |
| 30 | 30 | 88.0 | 347 |
| 30 | 30 | 88.7 | 326 |
| 30 | 33 | 95.6 | 128 |
| 30 | 33 | 93.6 | 185 |
| 30 | 45 | 99.0 | 28 |
| 30 | 45 | 98.9 | 30 |
| 30 | 60 | 98.9 | 31 |
| 30 | 60 | 98.9 | 31 |

| Sulfate (mmol/L) | 2 (mmol/L) | % Sulfate Removed | Sulfate Left (mg/L) |
|---|---|---|---|
| 30 | 15 | 48.41 | 1487 |
| 30 | 15 | 48.57 | 1482 |
| 30 | 30 | 93.28 | 194 |
| 30 | 30 | 94.41 | 161 |
| 30 | 33 | 99.72 | 8 |
| 30 | 33 | 99.60 | 12 |
| 30 | 45 | 99.94 | 1.7 |
| 30 | 45 | 99.94 | 1.7 |
| 30 | 60 | 99.95 | 1.5 |
| 30 | 60 | 99.95 | 1.5 |

The invention can be broadly applied to sulfate removal from aqueous solutions of various compositions, as well as from insoluble solids (e.g., sulfate scale) or solid suspensions (e.g., sulfate-containing solid suspensions in blackstrap molasses). Dissolution of insoluble sulfate salts, such as calcium sulfate (CaSO$_4$), can be achieved in a two-step process consisting of sequential dissolution of calcium and sulfate ions.

Figure 5:
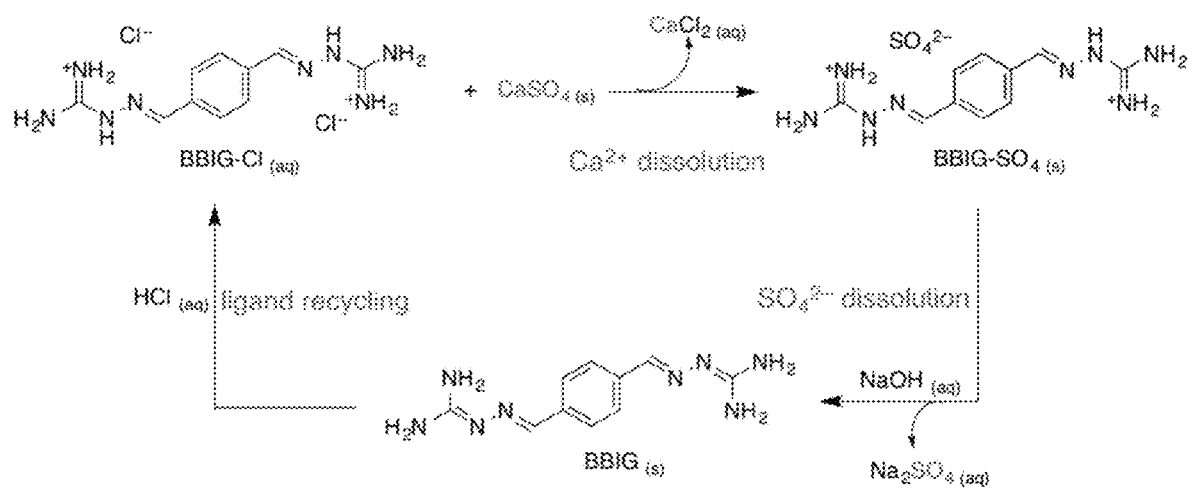
FIG. 5. Schematic diagram showing a CaSO$_4$ dissolution cycle using the BBIG compound, starting with BBIG-Cl.

An example of sulfate removal from a calcium sulfate suspension is shown schematically in FIG. 5. In the first step, the initial CaSO$_4$ solid is treated with an aqueous chloride salt of the compound that results in crystallization of the guanidinium sulfate salt and release of the calcium ions in solution, as soluble CaCl$_2$. In the second step, the insoluble guanidinium sulfate salt is treated with sodium hydroxide base to neutralize the guanidinium cations and release the sulfate ions in solution, as soluble Na$_2$SO$_4$. The resulting solid guanidine compound is then recycled and converted back into guanidinium chloride with aqueous HCl, so it can be reused in another CaSO$_4$ dissolution cycle. Thus, the entire process is done in water (no organic solvents used), and the only chemicals consumed in the overall process are NaOH and HCl, resulting in two aqueous waste streams consisting of calcium chloride and sodium sulfate. The unique aspect of this invention is the employment of a crystallization process to achieve dissolution of CaSO$_4$. Also, this approach is based on anion chelation by guanidinium groups rather than the more common metal chelation, which may be prone to interference from other metals in solution. The particular process shown in FIG. 5 employs the 1,4-benzene-bis(iminoguanidine) compound (BBIG) that has herein been found to form a sulfate salt (BBIG-SO4) of extremely low aqueous solubility. Single crystal X-ray diffraction indicated that this salt is hydrated by two water molecules in the crystalline state (FIG. 1A). The water-soluble chloride salt of this guanidine compound (BBIG-Cl) reacts with a suspension of CaSO$_4$ in water and forms crystalline BBIG-SO$_4$, while the calcium cations are released into the aqueous solution as CaCl$_2$. In the preliminary tests, the reaction was run overnight at room temperature and pH 6-7, and was monitored by powder X-ray diffraction, which confirmed the complete conversion of solid CaSO$_4$(H$_2$O)$_2$ into crystalline BBIG-SO$_4$(H$_2$O)$_2$. Subsequently, the crystals of BBIG-SO$_4$ were suspended in 10% aqueous sodium hydroxide and stirred at room temperature for two hours to yield solid BBIG (confirmed by X-ray diffraction as BBIG(H$_2$O)$_2$) and aqueous sodium sulfate. Finally, the recovered BBIG was converted back into the chloride salt by treatment with aqueous hydrochloric acid and recycled for another CaSO$_4$ dissolution cycle.

Direct Air Capture of Carbon Dioxide

Negative emissions, i.e. the net removal of greenhouse gases from the atmosphere, are now considered essential for stabilizing the global temperature at an optimal level. Direct air capture (DAC) of carbon dioxide from ambient air is one of the few available options for lowering the atmospheric CO$_2$ concentration, but existing technologies tend to be energy demanding and prohibitively expensive. Herein we report an effective and sustainable approach to DAC using the above-described bis-iminoguanidine and bis-iminoguanidinium compounds according to Formulas (1) and (1a), and more specifically, compounds 1 and 2.

Direct air capture of CO$_2$ with glycine and sarcosine: The CO$_2$ absorption from air was carried out with an Envion Humidiheat™ household air humidifier. The humidifier consists of a reservoir with a capacity of ~2 L, a rotating wick, which is made of a porous fabric that absorbs the liquid from the reservoir and provides a larger surface area, and a fan. The reservoir was filled with 1.5 L aqueous solutions of glycine or sarcosine (1 M) and KOH (1 M) and the fan was run on slow setting, corresponding to an air flow rate of 3.8±0.2 m/s. The capture experiments were run at ambient temperature (21±1° C.). However because of the water evaporation, the solution temperature was lower, averaging 16±1° C. The reservoir was replenished periodically with H$_2$O to compensate for the evaporated water (on average the evaporation rate was 100 mL/h) and keep the amino acid concentration as constant as possible. The change in the pH of the amino acid solution was monitored in situ with a glass electrode. The amount of CO$_2$ absorbed was monitored by withdrawing 300 μL samples and analyzing their carbonate and carbamate content by ion chromatography (IC) and $^1$H NMR spectroscopy, respectively. For NMR analyses, 900 μL of D$_2$O was added to 100 μL of the samples, whereas for the IC analyses, the samples were diluted 10-300 fold to bring the carbonate concentration in the 30-300 ppm range.

Regeneration of the amino acid sorbents with PyBIG: All regenerations were carried out at 25° C. in a thermostated oven. The amino acid solutions (5 mL) were placed in 15 mL polypropylene centrifuge tubes and PyBIG.2.5H$_2$O was added as a solid. The amount of PyBIG added varied with the CO$_2$ loading of the solution; the optimum amount was found to be 0.5 molar equivalents relative to the CO$_2$ absorbed (moles CO2/moles PyBIG=2). The resulting suspensions were mixed on a rotating wheel at 60 rpm to allow for a good contact between the two phases. Sub-samples were withdrawn hourly for the first 4 hours and then overnight. Each time, the tubes were centrifuged at 4000 rpm for 3 to 4 minutes depending on the thickness of the slurry. 50 μL of solution was then withdrawn using a micropipette to prepare the NMR and IC samples. For NMR analyses, 10 μL of the recovered solutions were mixed with 500 μL of D$_2$O, and for IC analyses, 5-10 μL of the solutions were diluted with 900 to 950 μL of H$_2$O. At the end of the regenerations, the final solids were filtered and analyzed by PXRD for phase identification.

Carbon dioxide release and regeneration of PyBIG using concentrated solar power: The CO$_2$ release from the PyBIGH$_2$(CO$_3$)(H$_2$O)$_4$ crystals was carried out by solar heating with a solar oven. The oven consists of a vacuum-insulated borosilicate tube placed in the focal point of two adjustable parabolic reflectors. The temperature inside the tube was monitored with a thermocouple. The PyBIGH$_2$(CO$_3$)(H$_2$O)$_4$ samples (0.038 g, 0.1 mmol) were loaded in 1 mL glass vials, which were placed inside the oven tube. The solar oven was then placed in the full sun and oriented to capture the maximum amount of sunlight. The temperature was ramped to the targeted values of 120° C., 140° C., 150° C., or 160° C. as fast as possible (typically within 3 to 10 minutes), then held within ±2° C. by intermittently moving the oven out of the sun, or/and closing the reflectors. The samples were subsequently removed from the tube, allowed to cool to room temperature, and weighed to determine their mass loss. The resulting yellow solids were analyzed by FTIR to confirm the disappearance of the carbonate and water peaks.

Figure 6:
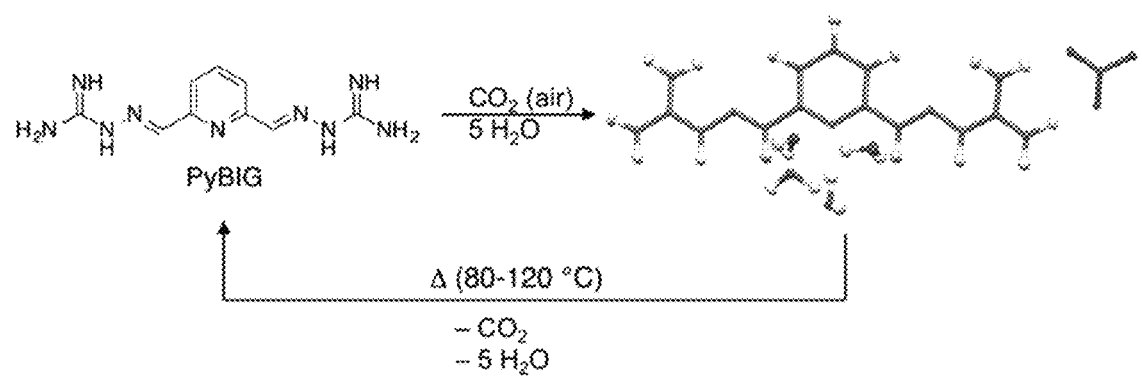
FIG. 6. Schematic diagram showing CO$_2$ capture from ambient air with aqueous PyBIG, leading to crystallization of PyBIGH$_2$(CO$_3$)(H$_2$O)$_4$ (single-crystal neutron structure shown). The $CO_2$ is released, and the PyBIG compound is regenerated quantitatively by relatively mild heating of the carbonate crystals.

Preliminary results indicated that aqueous 2,6-pyridine-bis(iminoguanidine) (PyBIG) captures CO$_2$ from ambient air and binds it as a crystalline tetrahydrated carbonate salt PyBIGH$_2$(CO$_3$)H$_2$O)$_4$. The CO$_2$ can be released by heating the carbonate crystals at relatively mild temperatures of 80-120° C., which regenerates the PyBIG compound quantitatively. A general schematic of the process is shown in FIG. 6. Examination of the PyBIGH$_2$(CO$_3$)(H$_2$O)$_4$ crystals by optical microscopy revealed that, upon heating in an oven at 120° C. for one hour, the crystals changed their color from cream to yellow to opaque. Thermogravimetric analysis coupled with mass spectrometry (TGA-MS) provided a more quantitative picture of the decomposition process. In a temperature-ramped TGA measurement, the PyBIGH$_2$(CO$_3$)(H$_2$O)$_4$ crystals lost 35.2% of their mass between 65 and 140° C., and the MS analysis confirmed the simultaneous evolution of water and CO$_2$. These measurements are consistent with the loss of one carbonate and two protons (as CO$_2$ and H$_2$O), and four additional water molecules, as expected from the crystal structure of PyBIGH$_2$(CO$_3$)(H$_2$O)$_4$ (35.1% theoretical mass loss). Similarly, the mass loss of the crystals heated in the oven for one hour at 120° C. (vide supra) was 34.3%, and the FTIR and NMR spectroscopic analysis of the resulting solid confirmed the complete disappearance of the carbonate peak and the regeneration of the anhydrous PyBIG compound. The TGA-MS analysis showed no decomposition of the regenerated compound up to 190° C., which provides a thermal stability window of at least 50° C. for compound recovery. Isothermal TGA runs at 120 and 100° C. showed complete loss of carbon dioxide and water after 60 and 150 minutes, respectively, with no additional mass loss after 5 hours. On the other hand, at 80° C. the decomposition reached 77% completion after 300 minutes. This corresponds to about an order of magnitude reduction in the decomposition temperature compared to inorganic carbonates, such as Na$_2$CO$_3$ or CaCO$_3$, involved in traditional DAC technologies.

The elementary steps involved in the CO$_2$ absorption and the overall reaction are represented by equations 1-7 as follows:

$$PyBIG_{(s)} \rightleftharpoons PyBIG_{(aq)} \tag{1}$$

$$PyBIG_{(aq)} + 2H_2O \rightleftharpoons PyBIG_2^{2+}{}_{(aq)} + 2HO^-{}_{(aq)} \tag{2}$$

$$CO_{2(g)} \rightleftharpoons CO_{2(aq)} \tag{3}$$

$$CO_{2(aq)} + HO^-{}_{(aq)} \rightarrow HCO_3^-{}_{(aq)} \tag{4}$$

$$HCO_3^-{}_{(aq)} + HO^-{}_{(aq)} \rightleftharpoons CO_3^{2-}{}_{(aq)} + H_2O \tag{5}$$

$$PyBIGH_2^{2+}{}_{(aq)} + CO_3^{2-}{}_{(aq)} + 4H_2O \rightleftharpoons PyBIGH_2(CO_3)(H_2O)_{4(s)} \tag{6}$$

$$PyBIG_{(s)} + CO_{2(g)} + 5H_2O \rightleftharpoons PyBIGH_2(CO_3)(H_2O)_{4(s)} \tag{7}$$

The crystalline PyBIG compound (as PyBIG.2H2O hydrate) first dissolves into water (equation 1), then the two guanidine groups become protonated by water molecules, generating the dicationic form of the compound (PyBIGH$_2^{2+}$) and HO$^-$ (equation 2). The hydroxide anions are the actual active species that react with the CO$_2$ absorbed from air (equation 3) and generate bicarbonate (equation 4) and carbonate anions (equation 5). Finally, the PyBIGH$_2^{2+}$ and CO$_3^{2-}$ ions crystallize with water into crystalline PyBIGH$_2$(CO$_3$)(H$_2$O)$_4$ (equation 6). The net reaction, shown in equation 7, corresponds to crystalline PyBIG converting into crystalline PyBIGH$_2$(CO$_3$)(H$_2$O)$_4$, in the presence of CO$_2$ and water, through dissolution/recrystallization.

Although PyBIG can capture CO$_2$ from ambient air according to equation 7, the reaction is too slow for practical considerations. The kinetics of CO$_2$ absorption by aqueous alkaline solutions, such as NaOH, have been found to be limited by a combination of the CO$_2$ diffusion into the aqueous solution (equation 3), and the reaction of CO$_2$ with HO$^-$ (equation 4). Thus, the rate of CO$_2$ absorption is controlled by the surface area of the air-liquid interface, and the solution alkalinity. For a typical 1 M solution of NaOH, the flux of CO$_2$ absorbed from air has been estimated around 30 μmol/m2/s (Zeman, F., Environ. Sci. Technol. 41, 7558-7563, 2007). However, compared to NaOH, PyBIG is significantly less alkaline. A saturated solution of PyBIG (~10 mM) has a pH of about 10, which corresponds to a rate of CO$_2$ reaction that is at least a couple orders of magnitude lower than for NaOH. Another constraint is that in a typical crystallization set-up the air-liquid contact area is relatively small, which further limits the CO$_2$ absorption rate.

Figure 7A:
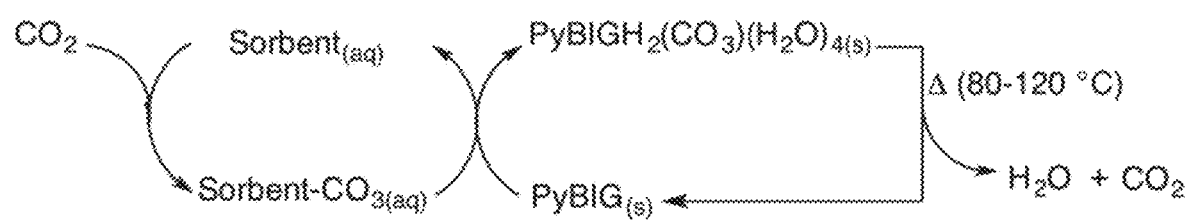
FIGS. 7A, 7B.

One possible solution to the slow CO$_2$ sorption problem is to combine the PyBIG crystallization with a traditional aqueous sorbent that absorbs atmospheric CO$_2$ relatively fast and converts it into carbonate. The solution is subsequently reacted with PyBIG to crystallize PyBIGH$_2$(CO$_3$)(H$_2$O)$_4$ and regenerate the sorbent. Finally, the carbonate crystals are filtered out of solution and heated in the solid state to release the CO$_2$ and regenerate the PyBIG compound, which can then be reused in another cycle. FIG. 7A provides a general schematic of the above concept. The advantage of such a hybrid approach to CO$_2$ capture, which combines room temperature absorption in the liquid phase with CO$_2$ release in the solid state, is that it benefits from the fast sorption kinetics of an aqueous sorbent while avoiding the energy penalty associated with heating aqueous solutions during regeneration. Furthermore, sorbent loss through evaporation and thermal degradation is minimized.

Figure 7B:
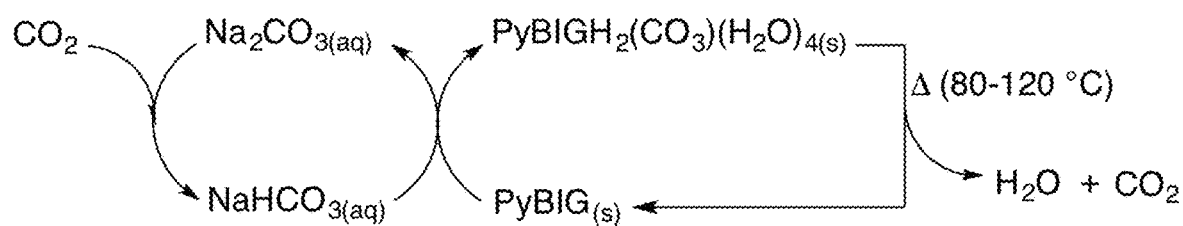

One approach to DAC with PyBIG is to combine the crystallization of PyBIGH$_2$(CO$_3$)(H$_2$O)$_4$ with the well-established carbonate/bicarbonate CO$_2$ capture cycle. A general schematic of the process is shown in FIG. 7B. The chemical reactions occurring in the carbonate/bicarbonate CO$_2$ capture cycle are shown in the following equations:

$$CO_3^{2-}+CO_2+H_2O \rightarrow 2HCO_3^- \quad \text{(Eq. 1)}$$

$$PyBIG_{(s)}+2HCO_3^-+4H_2O \rightarrow PyBIGH_2(CO_3)(H_2O)_{4(s)}+CO_3^{2-} \quad \text{(Eq. 2)}$$

In this approach, CO$_2$ sorption by an alkali carbonate solution (Eq. 1) is followed by the reaction of the resulting bicarbonate with PyBIG to crystallize PyBIGH$_2$(CO$_3$)(H$_2$O)$_4$ and regenerate the carbonate sorbent (Eq. 2). Finally, thermal decomposition of PyBIGH$_2$(CO$_3$)(H$_2$O)$_4$ regenerates the PyBIG compound and releases the CO$_2$. To demonstrate the feasibility of this approach, solid PyBIG (1 mol equiv) was suspended in a solution of 1 M NaHCO$_3$ (5-6 mol equiv) and the slurry was stirred at room temperature for four hours. The resulting mixture was filtered, and the separated crystalline solid was confirmed by PXRD and FTIR to be PyBIGH$_2$(CO$_3$)(H$_2$O)$_4$. Subsequent heating of the carbonate crystals in the oven for one hour at 120° C. regenerated the PyBIG solid, which was recycled back into the original sodium bicarbonate solution. The entire carbonate separation cycle was run three times, with observed yields for PyBIGH$_2$(CO$_3$)(H$_2$O)$_4$ crystallization of 99.0±0.4%, 97.2±0.6%, and 91.4±0.4%, corresponding to the first, second, and third cycle, respectively. The regeneration of the PyBIG compound was nearly quantitative in each cycle. The slight decrease in the crystallization yield observed in the later cycles is explained by the gradual increase in the solution alkalinity (initial pH 8.5, final pH 10.5) as a result of the increasing CO$_3^{2-}$/HCO$_3^-$, ratio. As more bicarbonate is converted into carbonate in each subsequent cycle, according to Eq. 2, the pH of the solution should eventually become high enough to inhibit the protonation of PyBIG, thereby decreasing the driving force for the crystallization of PyBIGH$_2$(CO$_3$)(H$_2$O)$_4$. This is corroborated by the FTIR analysis of the isolated solid, which showed preponderantly the carbonate phase after the first two cycles, but a mixture of carbonate and free PyBIG compound after the third cycle.

After considering several potential sorbents, two simple amino acids, glycine and sarcosine, were selected for the DAC system. Aqueous amino acids have a number of positive attributes that make them promising candidates for DAC. They have fast CO$_2$ sorption kinetics, on par with or surpassing more traditional sorbents like monoethanolamine or NaOH. Amino acids are non-volatile, non-corrosive, environmentally friendly, and relatively inexpensive. They are also less susceptible to oxidation than amines. While amino acid sorbents have been employed in CO$_2$ scrubbing from flue gas, their use in DAC remains unexplored. The chemical reactions involved in the CO$_2$ absorption with amino acids and in the sorbent regeneration with PyBIG are depicted in equations 8-10 below, using glycine as a representative example.

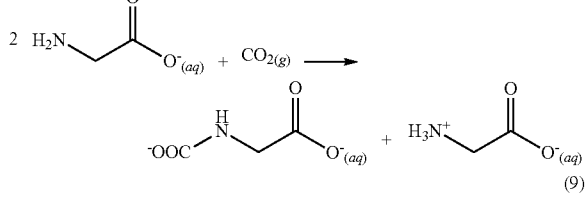

(8)

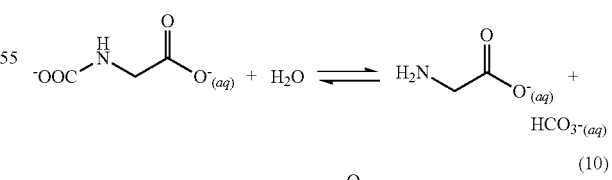

(9)

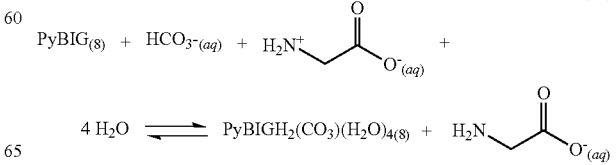

(10)

First, the anionic form of glycine (glycinate) reacts with $CO_2$ and generates the corresponding carbamic acid, which is deprotonated by a second equivalent of glycine to generate the carbamate and the zwitterionic glycine (equation 8). The carbamate is subsequently hydrolyzed to glycinate and bicarbonate (equation 9). Finally, PyBIG deprotonates the bicarbonate and the zwitterionic glycine and crystallizes as $PyBIGH_2(CO_3)(H_2O)_4$ while regenerating the glycinate sorbent (equation 10). Note that adding the three reactions together leads to the same overall reaction represented by equation 7. However, the kinetics of the amino acid-mediated DAC process are expected to be significantly faster than with PyBIG alone.

In addition to fast kinetics for the $CO_2$ reaction with the sorbent, a practical DAC system requires effective mass transfer of $CO_2$ from air into the sorbent solution, which in turn requires an efficient contactor that maximizes the air-liquid interfacial area. Unlike $CO_2$ capture from flue gas, which is typically done with a packed absorption column that is designed to operate at high liquid/gas ratios and with a high degree of $CO_2$ removal, DAC is more suitably done in a more open system with contactors that are optimized to ingest large volumes of ambient air, in many ways similar in design with large-scale cooling towers. For the purpose of this study, which is a small-scale proof of principle for DAC with the amino acid/guanidine system, a household humidifier was used as an air-liquid contactor. Like a cooling tower, an air humidifier is designed to maximize the air-water contact area, and by replacing the water with an amino acid solution, it effectively becomes a DAC absorber.

Thermodynamic Analysis

Once the basic design elements were established, the next important step was to determine the thermodynamics of the $CO_2$ absorption and desorption, as well as of sorbent regeneration, which define the energy and efficiency boundaries for the DAC system. The energetics of the $CO_2$ absorption (equation 7) can be obtained by adding up the energetics of the elementary reactions represented by equations 1-6. The enthalpies of $CO_2$ hydration (equation 3) and of reaction with $HO^-$ to generate bicarbonate (equation 4) are already known. The heat of bicarbonate deprotonation by $HO^-$ to make $CO_3^{2-}$ (equation 5) can also be calculated from published thermodynamic data on carbonate protonation and water ionization. The remaining enthalpies for the reactions involving PyBIG and $PyBIGH_2(CO_3)(H_2O)_4$ were determined as part of this study. The enthalpies of PyBIG dissolution (equation 1) and $PyBIGH_2(CO_3)(H_2O)_4$ crystallization (equation 6) were obtained by variable-temperature solubility measurements of the two solids and van't Hoff analyses). Finally, the enthalpies of PyBIG protonation (equation 2) were obtained from variable-temperature pKa measurements by potentiometric titrations and van't Hoff analyses. The corresponding ΔH values for reactions 1-6 are listed in Table 4 below. Adding up these values results in an overall enthalpy of $CO_2$ absorption by PyBIG of −70.7 kJ/mol.

TABLE 4

Reaction enthalpies for the corresponding elementary steps involved in DAC with PyBIG.

| Reaction | ΔH (kJ/mol) | Reference |
|---|---|---|
| 1 | 42.5 | This study |
| 2 | 43.6[a] | This study |
| 3 | −19.4 | 29 |
| 4 | −50 | 30 |
| 5 | −40.4 | 31, 32 |
| 6 | −47 | This study |

[a]The enthalpy for reaction 2 is composed of the sum of the fist (−31 kJ/mol) and second (−37 kJ/mol) protonanon enthalpies of PyBIG minus twice the enthalpy of ionization of water (55.8 kJ/mol).

Although the $CO_2$ desorption could theoretically be achieved by running reactions 1-6 in reverse order according to the principle of microscopic reversibility, in reality it would not be feasible as reaction 4 is practically irreversible. Such an approach would also defeat the purpose of avoiding heating the aqueous sorbent. Instead, once the loading is complete, the crystalline $PyBIGH_2(CO_3)(H_2O)_4$ is removed from solution and heated in the solid state to release the $CO_2$ gas and the water vapors. Given the completely different conditions involved, such a gas-solid process must have different energetics compared to the gas-liquid-solid process involved in $CO_2$ absorption. In order to determine the enthalpy of $CO_2$ release, differential scanning calorimetry (DSC) was employed. DSC is a common technique used in thermal analysis of solids. The DSC curve (showed a series of endothermic events between 80 and 140° C., corresponding to the release of water and $CO_2$ as previously found by thermogravimetric analysis (Seipp et al., Angew. Chem. Int. Ed. 56, 1042-1045, 2017). Unfortunately, the extensive overlap between the peaks prevented a determination of the heats associated with each thermal event. Instead, all the peaks were integrated together to obtain the overall enthalpy of desorption for $PyBIGH_2(CO_3)(H_2O)_4$, which amounts to 223±4 kJ/mol. While the overall reaction is highly endothermic, it must be taken into account that for each mole of $CO_2$ released, there are five moles of water that need to be vaporized. As the enthalpy of vaporization for water is 40.65 kJ/mol, more than 90% of the enthalpy of desorption is used for water evaporation. This represents a significant energy penalty that must be accounted for, and which encourages the use of renewable sources of energy, such as concentrated solar power (vide infra), to make the overall DAC process energy more sustainable.

In addition to the enthalpies of CO2 absorption and release, another important thermodynamic parameter is the equilibrium constant for the amino acid regeneration reaction (equation 10), which defines the efficiency limit for sorbent regeneration. In the regeneration reaction, the solid PyBIG has to dissolve into the sorbent solution, deprotonate the amino acid and the bicarbonate ion, and crystallize as $PyBIGH_2(CO_3)(H_2O)_4$. In the case of the glycine sorbent, the equilibrium constant for the regeneration reaction (log Kreg) is defined by equation 11 as follows:

$$\log K_{reg} = \log K_{sp}(PyBIG) - \log K_{sp}(PyBIGH_2(CO_3)(H_2O)_4) - pK_a(Gly) - pK_a(HCO_3^-) + pK_{a1}(PyBIG) + pK_{a2}(PyBIG) \quad (11)$$

Thus, the amino acid regeneration is driven by the difference in solubility between PyBIG and $PyBIGH_2(CO_3)(H_2O)_4$, as well as the difference in basicity between glycine and bicarbonate on one hand, and PyBIG on the other hand. The pKa values at 25° C. for the two guanidinium groups of PyBIG, determined by potentiometric titration, are 7.6 and 8.7. On the other hand, the pKa values of glycine and bicarbonate are 9.5 and 10.3, respectively (Yang N. et al., Ind. Eng. Chem. Res. 53, 12848-12855, 2014). Thus, PyBIG is not sufficiently basic to drive the regeneration equilibrium to the right, and therefore the main driving force has to come from the solubility difference between PyBIG and PyBIGH$_2$(CO$_3$)(H$_2$O)$_4$. A preliminary estimated value of $1.0 \times 10^{-8}$ is given for the solubility product of PyBIGH$_2$(CO$_3$)(H$_2$O)$_4$. As part of this study, determination of a more accurate value became possible as the exact specification of PyBIG in solution could now be obtained based on the measured pKa values of PyBIG, resulting in a revised K, for PyBIGH$_2$(CO$_3$)(H$_2$O)$_4$ of $1.0 \pm 0.3 \times 10^{-9}$ at 25° C. This corresponds to a very insoluble carbonate salt, on a par with the natural calcite mineral ($K_{sp} = 3.3 \times 10^{-9}$). By comparison, the measured $K_{sp}$ of PyBIG at the same temperature is $1.0 \pm 0.3 \times 10^{-2}$. Thus, under ideal conditions, $\log K_{reg} = 3.5$, which predicts a very efficient amino acid regeneration. However, under realistic conditions involving high ionic strength solutions that can significantly impact the solubilities of the various species involved through ion pairing, salting out, etc., the observed regeneration efficiency may actually be less than ideal.

Carbon Dioxide Absorption with Aqueous Glycine and Sarcosine

Figure 8A:
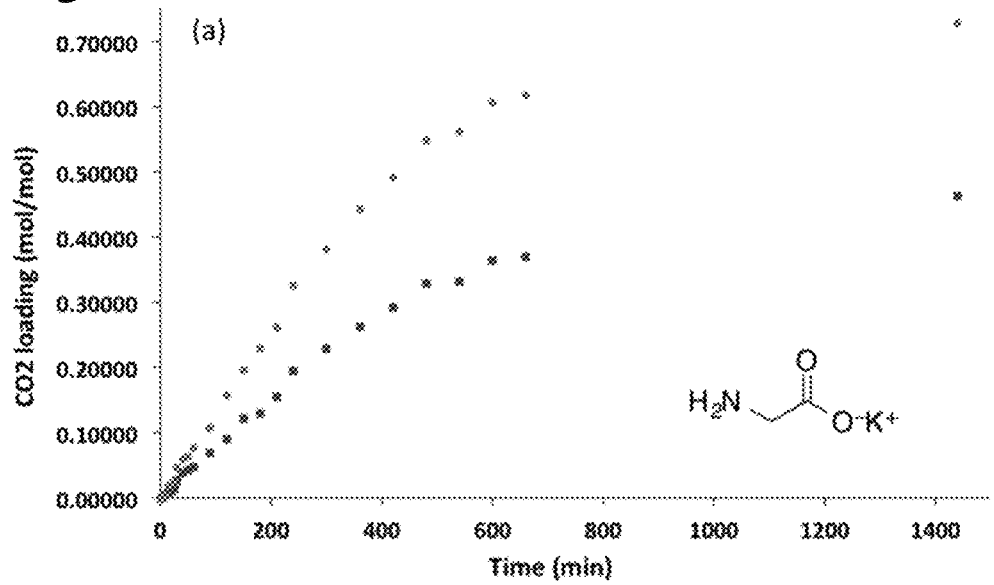
FIGS. 8A, 8B. Chart showing absorption of atmospheric $CO_2$ into 1 M aqueous solutions of glycine/KOH (FIG. 8A) and sarcosine/KOH (FIG. 8B) as a function of time. Squares and dots correspond to carbonate and total $CO_2$ (carbonate+carbamate) loadings, respectively.
Figure 8B:
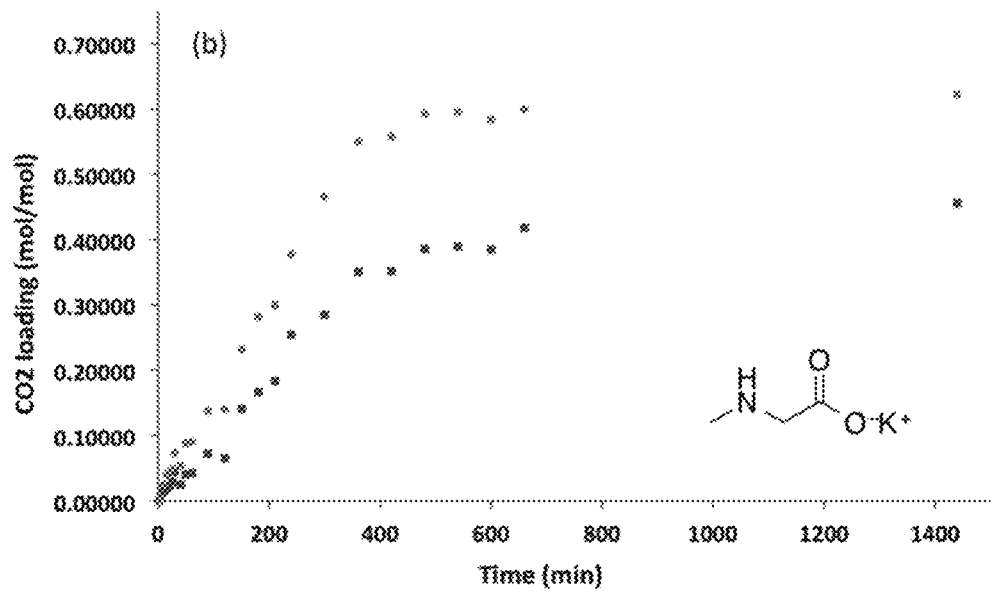

The direct air capture of CO$_2$ in this study was done with an air humidifier shown using aqueous amino acid sorbents (as potassium salts). The loading of CO$_2$ into 1 M aqueous solutions of potassium glycinate and sarcosinate as a function of time is shown in FIG. 8. The extent of CO$_2$ absorption was monitored in situ by pH measurements, and ex situ by IC and $^1$HNMR to determine the amounts of carbonate and carbamate formed. The sorption experiments were run for 24 hours and the results are summarized in Table 5 below.

TABLE 5

Carbon dioxide loading values for 1M aqueous solutions of potassium glycinate and sarcosinate after 24 hours

| Sorbent | pH (initial/final) | Carbonate (M) | Carbamate (M) | Total CO$_2$ (M) |
|---|---|---|---|---|
| Glycine (1M) | 12.31/9.52 | 0.46 | 0.27 | 0.73 |
| Sarcosine (1M) | 12.92/9.99 | 0.46 | 0.17 | 0.63 |

The initial CO$_2$ absorption rate is slightly higher for sarcosine than glycine, possibly reflecting the more alkaline nature of the former. However, the absorption rate for sarcosine slows down considerably and levels off after about 6 hours, while the corresponding absorption rate for glycine slows down more gradually. While the reaction rates of CO$_2$ with both sarcosine and glycine are expected to be quite high (18.6 and 13.9 kM/s, respectively, at 25° C.), the much slower rates of CO$_2$ absorption observed presumably reflect the relatively limited (<1 m$^2$) air-water interfacial area available with the air humidifier employed in this study. After 24 hours, the total CO$_2$ loading for glycine (0.73 mol/mol) was slightly higher than for sarcosine (0.63 mol/mol). The difference can be accounted for by the larger amount of carbamate formed with glycine (0.27 M) compared to sarcosine (0.17 M).

Sorbent Regeneration by Carbonate Crystallization with PyBIG

Figure 9:
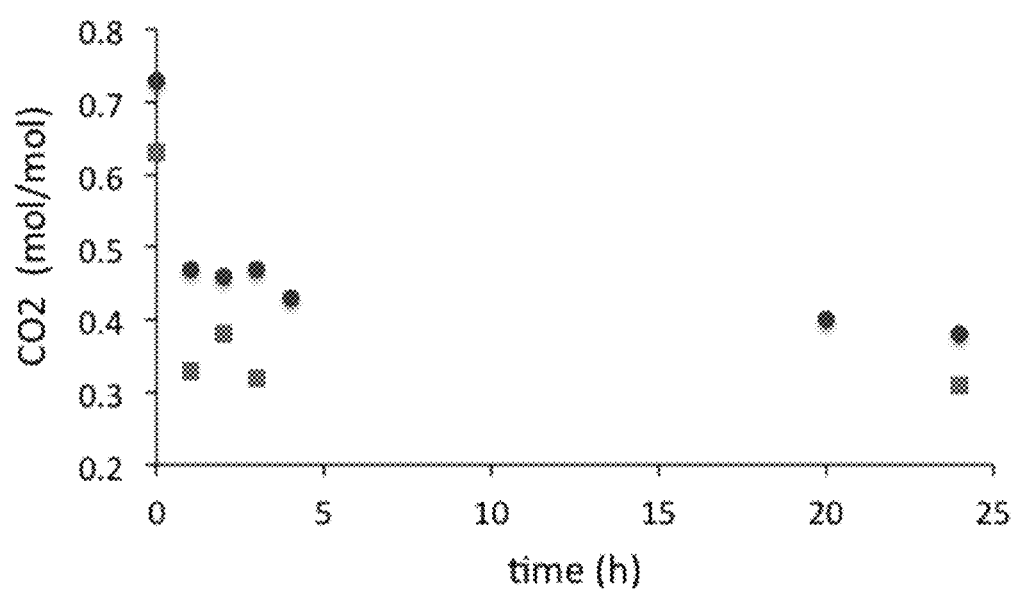
FIG. 9. Decrease in the total $CO_2$ concentration of the loaded glycine (dots) and sarcosine (squares) sorbents during regeneration with PyBIG.

The CO$_2$-loaded sorbents were stirred with a suspension of PyBIG (0.5 molar equivalents relative to CO$_2$) at room temperature, which resulted in crystallization of PyBIGH$_2$(CO$_3$)(H$_2$O)$_4$ and regeneration of the anionic forms of the amino acids, according to equation 10. The formation of crystalline PyBIGH$_2$(CO$_3$)(H$_2$O)$_4$ was confirmed by powder X-ray diffraction (PXRD), which revealed after 24 hours a mixture of PyBIG.2.5H$_2$O and the carbonate salt. The concentrations of carbonate and carbamate in the amino acid solutions were monitored by IC and NMR, respectively, and the decrease in total CO$_2$ loading as a function of time is plotted in FIG. 9. The results after 24 hours regeneration time are summarized in Table 6 below.

TABLE 6

Regeneration results for the 1M aqueous solutions of potassium glycinate and sarcosinate after stirring with a suspension of PyBIG (0.5 molar equiv) for 24 hours.

| Sorbent | pH (initial/final) | Carbonate (M) | Carbamate (M) | Total CO$_2$ (M) |
|---|---|---|---|---|
| Glycine (1M) | 9.63/10.33 | 0.33 | 0.05 | 0.38 |
| Sarcosine (1M) | 9.99/10.53 | 0.29 | 0.03 | 0.32 |

Most of the CO$_2$ from each sorbent is released within an hour, and longer regeneration times only led to marginal improvements. The cyclic capacity, defined as the difference between the maximum CO$_2$ loading observed after absorption and the minimum CO$_2$ loading measured after regeneration, is 0.35 and 0.31 mol/mol for the glycine and sarcosine sorbents, respectively.

Regeneration of the amino acid sorbents can also be achieved in a traditional fashion, by boiling the aqueous solutions under reflux. After one hour of refluxing, the total CO$_2$ concentrations in the glycine and sarcosine sorbents dropped to 0.42 and 0.32 M, respectively, which are comparable with the corresponding values observed in the regenerations using PyBIG. With longer reaction times the regeneration under reflux outperforms the regeneration with PyBIG, with the total CO$_2$ concentrations in solution dropping to 0.26 and 0.17 M after 4 hours of refluxing the glycine and sarcosine solutions, respectively. However, such long refluxing times are expected to come at a cost in terms of energy consumption and sorbent degradation.

Carbon Dioxide Release and Regeneration of the PyBIG Compound with Concentrated Solar Power This preliminary study indicated that the PyBIGH$_2$(CO$_3$)(H$_2$O)$_4$ crystals release the CO$_2$ and water vapor upon mild heating at temperatures of 80-120° C., and regenerate the PyBIG compound quantitatively. However, considering this transformation is highly endothermic, the possibility of using concentrated solar power to render the process more energy sustainable was explored. For the initial small-scale proof of concept, a solar oven (FIG. 6) was used to heat the PyBIGH$_2$(CO$_3$)(H$_2$O)$_4$ samples (38 mg, 0.1 mmol) at four different temperatures ranging between 120 and 160° C., monitoring the extent of the reactions by the samples' weight loss (Table 7 below). FTIR analyses also corroborated the release of CO$_2$, most evidently noticeable by the disappearance of the strong peak at 1361 cm$^{-1}$ corresponding to the stretching mode of the carbonate anion. Thus, these results demonstrate that concentrated solar power can effectively release the CO$_2$ from the carbonate crystals and regenerate the PyBIG compound quantitatively.

TABLE 7

CO2 release from PyBIGH$_2$(CO$_3$)(H$_2$O)$_4$ and regeneration of PyBIG by heating with concentrated solar power. All measurements were done with 38 mg (0.1 mmol) samples. The theoretical weight loss for a quantitative yield is 13.4 mg (35.1%), corresponding to 0.1 mmol CO$_2$ and 0.5 mmol H$_2$O. Experimental uncertainties: T = ±2° C.; Δm =±1 mg (±2.6%)

| T (° C.) | Heating time (min) | Δm (mg) | Δm/m$_i$ (%) |
|---|---|---|---|
| 120 | 30 | −12 | −31.6 |
| 140 | 10 | −13 | −34.2 |
| 150 | 5 | −12 | −31.6 |
| 160 | 2 | −14 | −36.8 |

CONCLUSIONS

This study demonstrated a small-scale DAC system using simple, off-the-shelf equipment and readily available chemicals. Effective CO$_2$ absorption with aqueous glycine and sarcosine sorbents using a household humidifier was followed by room temperature crystallization of a guanidinium carbonate salt of very low aqueous solubility, and CO$_2$ desorption from the carbonate crystals using concentrated solar power. This approach combines the benefits of an aqueous sorbent, such as fast CO$_2$ absorption rates, easy handling, and low maintenance, with the advantages of solid-state CO$_2$ desorption that avoids much of the energy penalty associated with heating and evaporating aqueous solutions, and minimizes sorbent degradation. Furthermore, the amino acid sorbents offer an environmentally friendly alternative to the more traditional sorbents, such as amines or NaOH. In addition to demonstrating the initial proof-of-concept, this study also identified a number of limitations for the current DAC system and provided guidelines for the design and optimization of future DAC technologies. First, while the amino acid sorbents react fast with CO$_2$, the air humidifier used in this study is not optimized for DAC as it provides a relatively small air-water interfacial area, which limits the overall CO$_2$ uptake rate. Also, as designed, the humidifier evaporates large amounts of water, which in the case of DAC is a disadvantage. Combining the amino acid sorbents with better air-liquid contactors that optimize the air-water interfacial area and minimize the water loss may lead to more efficient DAC systems. Second, while sorbent regeneration and carbonate crystallization with PyBIG is adequate, with observed cyclic capacities of 0.3-0.35 mol/mol, the regeneration process could be significantly improved by replacing the PyBIG compound with a more soluble and more alkaline (higher pKa for the guanidine groups) analogue that would push the equilibrium for the regeneration reaction further to the right, according to equation 11. Finally, although the CO$_2$ desorption from crystalline PyBIGH$_2$(CO$_3$)(H$_2$O)$_4$ avoids much of the energy penalty associated with heating and evaporating aqueous solutions, the enthalpy of desorption of the carbonate crystals is strongly endothermic, mainly due to the inclusion of water in the crystals. Engineering carbonate crystals that are anhydrous, or can release the CO$_2$ at lower temperatures to avoid water vaporization, may improve the energy efficiency of the DAC process. On the other hand, employing renewable energy sources, such as concentrated solar power, as demonstrated in this study, or low-grade waste heat, may alleviate much of this issue.

While there have been shown and described what are at present considered the preferred embodiments of the invention, those skilled in the art may make various changes and modifications which remain within the scope of the invention defined by the appended claims.

What is claimed is:

1. A method for removing an inorganic oxyanion from an aqueous source containing an inorganic oxyanion salt, the method comprising:
   (i) dissolving an oxyanion precipitating compound into said aqueous source containing said inorganic oxyanion salt to result in precipitation of an inorganic oxyanion compound salt of said oxyanion precipitating compound; and
   (ii) removing said inorganic oxyanion compound salt from said water containing the inorganic oxyanion salt to result in water reduced in concentration of said inorganic oxyanion salt;

wherein said oxyanion precipitating compound has the following formula:

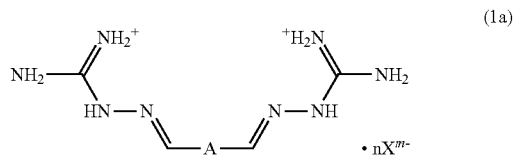

(1a)

wherein:
A is a ring-containing moiety;
one or more of the hydrogen atoms in Formula (1a) may be replaced with one or more methyl groups;
X$^{m-}$ is an anionic species with a magnitude of charge m, where m is an integer of at least 1, provided that X$^{m-}$ is an anionic species exchangeable with the inorganic oxyanion in said inorganic oxyanion salt in said aqueous source before said oxyanion precipitating compound contacts said inorganic oxyanion salt in step (i), and X$^{m-}$ is said inorganic oxyanion in the inorganic oxyanion compound salt of said oxyanion precipitating compound; and
n is an integer of at least 1;
provided that n×m=2.

2. The method of claim 1, wherein said inorganic oxyanion is selected from the group consisting of sulfate, nitrate, chromate, selenate, phosphate, arsenate, carbonate, bicarbonate, and perchlorate.

3. The method of claim 1, wherein said inorganic oxyanion is sulfate.

4. The method of claim 1, wherein A is a monocyclic ring.

5. The method of claim 4, wherein said monocyclic ring is a five-membered, six-membered, or seven-membered ring.

6. The method of claim 1, wherein A is a carbocyclic ring or ring system.

7. The method of claim 6, wherein said carbocyclic ring or ring system is unsaturated.

8. The method of claim 7, wherein A comprises a benzene ring.

9. The method of claim 1, wherein A is a heterocyclic ring or ring system.

10. The method of claim 9, wherein said heterocyclic ring or ring system is unsaturated.

11. The method of claim 9, wherein said heterocyclic ring or ring system contains at least one nitrogen ring atom.

12. The method of claim 11, wherein A comprises a pyridine ring.

13. A method for removing carbon dioxide from a gaseous source, the method comprising:
(i) contacting said gaseous source with an aqueous solution containing a carbon dioxide complexing compound to result in precipitation of a carbonate or bicarbonate salt of said carbon dioxide complexing compound; and
(ii) removing said carbonate or bicarbonate salt from said aqueous solution;
wherein said carbon dioxide complexing compound has the following formula:

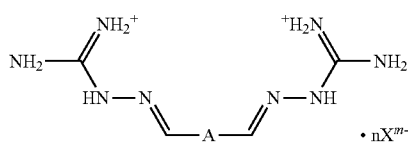
(1a)

wherein:
A is a ring-containing moiety;
one or more of the hydrogen atoms in Formula (1a) may be replaced with one or more methyl groups;
$X^{m-}$ is an anionic species with a magnitude of charge m, where m is an integer of at least 1, provided that $X^{m-}$ is hydroxide in said carbon dioxide complexing compound before said carbon dioxide complexing compound is contacted with carbon dioxide in step (i), and $X^{m-}$ is carbonate or bicarbonate in said carbonate or bicarbonate salt; and
n is an integer of at least 1;
provided that n×m=2.

14. The method of claim 13, wherein A is a monocyclic ring.

15. The method of claim 14, wherein said monocyclic ring is a five-membered, six-membered, or seven-membered ring.

16. The method of claim 13, wherein A is a carbocyclic ring or ring system.

17. The method of claim 16, wherein said carbocyclic ring or ring system is unsaturated.

18. The method of claim 17, wherein A comprises a benzene ring.

19. The method of claim 13, wherein A is a heterocyclic ring or ring system.

20. The method of claim 19, wherein said heterocyclic ring or ring system is unsaturated.

21. The method of claim 19, wherein said heterocyclic ring or ring system contains at least one nitrogen ring atom.

22. The method of claim 19, wherein A comprises a pyridine ring.

* * * * *

UNITED STATES PATENT AND TRADEMARK OFFICE
CERTIFICATE OF CORRECTION

PATENT NO. : 10,633,332 B2
APPLICATION NO. : 16/129979
DATED : April 28, 2020
INVENTOR(S) : Custelcean et al.

Page 1 of 1

It is certified that error appears in the above-identified patent and that said Letters Patent is hereby corrected as shown below:

On the Title Page

Page 2, Related U.S. Application Data, should read:
(60) Provisional application No. 62/422,138, filed on Nov. 15, 2016, provisional application No. 62/459,118, filed on Feb. 15, 2017, provisional application No. 62/422,142, filed on Nov. 15, 2016, provisional application No. 62/514,997, filed on Jun. 5, 2017.

Signed and Sealed this
Eighteenth Day of August, 2020

Andrei Iancu
*Director of the United States Patent and Trademark Office*